US005821219A

United States Patent [19]
Grandy et al.

[11] Patent Number: 5,821,219
[45] Date of Patent: Oct. 13, 1998

[54] OPIOID ANTAGONISTS AND METHODS OF THEIR USE

[75] Inventors: David K. Grandy; Judith E. Grisel, both of Portland, Oreg.; Jeffrey S. Mogil, Vancouver, Wash.

[73] Assignee: Oregon Health Sciences University, Portland, Oreg.

[21] Appl. No.: 553,058

[22] Filed: Nov. 3, 1995

Related U.S. Application Data

[63] Continuation of Ser. No. 514,451, Aug. 11, 1995.
[51] Int. Cl.$^6$ .......................... A61K 38/03; G07K 14/575
[52] U.S. Cl. .............................................. 514/2; 530/350
[58] Field of Search ................................. 574/2; 530/350

[56] References Cited

U.S. PATENT DOCUMENTS

| | | | |
|---|---|---|---|
| 4,582,820 | 4/1986 | Teng ......................................... | 424/25 |
| 4,683,195 | 7/1987 | Mullis et al. ............................... | 435/6 |
| 4,683,202 | 7/1987 | Mullis .................................... | 435/91.2 |
| 5,512,578 | 4/1996 | Crain et al. ............................. | 514/282 |

FOREIGN PATENT DOCUMENTS

| | | |
|---|---|---|
| WO/91/00736 | 1/1991 | WIPO . |
| WO/95/07983 | 3/1995 | WIPO . |

OTHER PUBLICATIONS

Brownstein et al., 1993, *Proc. Natl. Acad. Sci. USA* 90:pp. 5391–5393.
Jaffe and Martin, 1990, "Opioid Analgesics and Antagonists", in Goodman and Gilman, eds., *The Pharmacological Basis of Therapeutics*, 8th ed. (Pergammon Press, Inc.: New York), Chapter 21, pp. 485–521.
Atherton et al., 1989, *Solid Phase Peptide Synthesis* (IRL Press: Oxford).
Sambrook et al., 1990, *Molecular Cloning: A Laboratory Manual* (Cold Spring Harbor Press: New York).
*Tissue Culture*, Academic Press, Kruse & Patterson, editors (1973).
Walters, "Computer–Assisted Modeling of Drugs", in Glegerman & Groves, eds., 1993, *Pharmaceutical Biotechnology*, Interpharm Press: Buffalo Grove, IL, pp. 165–174.
Eisenberg et al., 1984, *J. Molec. Biol.* 179:pp. 125–142.
Chen and Okayama, 1987, *Molec. Cell Biol.* 7:pp. 2745–2752.
Bunzow et al., 1988, *Nature* 336:pp. 783–787.
Rappolee et al., 1988, *Science* 241:pp. 1823–1825.
Zubay, *Biochemistry* 2d ed., 1988, MacMillan Publishing: New York, p. 33.
Hunter and Greenwood, 1962, *Nature* 194:p. 495.
Nelson, 1987, *Anal. Biochem.* 165:p. 287.
Bosworth and Towers, 1989, *Nature* 341:p. 167.
Irwin, 1968, *Psychopharmacologia* 13:p. 222.
Chen et al., "Molecular Cloning and Functional Expression of a $\mu$–Opioid Receptor from Rat Brain," *Molec. Pharmacol.* 44:8–12 (1993).

Yasuda et al., "Cloning and functional comparison of $\kappa$ and $\delta$ opioid receptors from mouse brain," *Natl. Acad. Sci. USA* 90:6736–6740 (1993).
Bzdega et al., "Regional expression and chromosomal location of the $\delta$ opiate receptor gene," *Proc. Natl. Acad. Sci. USA* 90: 9305–9309 (1993).
Brownstein, "A brief history of opiates, opioid peptides, and opioid receptors," *Proc. Natl. Acad. Sci. USA* 90:5391–5393 (1993).
DiChiara et al., "Neurobiology of opiate abuse," *Trends in Pharmacol. Sci.* 13:185–193 (1992).
Manackjee et al., "Nonconventional opioid binding sites mediate growth inhibitory effects of methadone on human lung cancer cells," *Proc. Natl. Acad. Sci USA* 89:1169–1173 (1992).
Kieffer et al., "The $\delta$–opioid receptor: Isolation of a cDNA by expression cloning and pharmacological characterization," *Proc. Natl. Acad. Sci. USA* 89:12048–12052 (1992).
Evans et al., "Cloning of Delta Opioid Receptor by Functional Expression," *Science* 258:1952–1955 (1992).
McKnight et al., "Opioid Receptors and their Ligands," *Neurotransmissions* 7:1–6 (1991).
Goldstein, "Binding selectivity profiles for ligands of multiple receptors types: focus on opiod receptors," *Trends in Pharmacol. Sci.* 8:456–459 (1987).
Kristensen et al., *Life Sciences* 56:45 (1995).
Fukuda et al., "Primary structures and expression from cDNAs of rat opioid receptor $\delta$–and $\mu$–subtypes," *FEBS Letters* 327:311 (1993).
Wang et al., "$\mu$–opiate receptor: cDNA cloning and expression," *Proc. Natl. Acad. Sci.* 90:10230 (1993).

(List continued on next page.)

*Primary Examiner*—Stephen Walsh
*Assistant Examiner*—Daryl K. Basham
*Attorney, Agent, or Firm*—Klarquist Sparkman Campbell Leigh & Whinston, LLP

[57] ABSTRACT

The present invention relates to a novel mammalian anti-opioid receptor protein (OFQR), peptide ligands (such as OFQ) that bind to OFQR, and methods of using the OFQ peptide and analogues to reverse the physiologic effects of opiates such as morphine. The isolation, characterization and pharmacological use of the endogenous peptide ligand is described. A particular embodiment of the OFQ peptide is a heptadecapeptide having an FGGF aminoterminal motif. The peptide specifically binds to an OFQ receptor protein heterologously expressed in mammalian cells. The peptide does not bind with high affinity to $\mu$, $\delta$ or $\kappa$ receptors, but it antagonizes opioid mediated effects (such as analgesia and hypothermia) without increasing nociceptive sensitivity. Tyrosine substitution variants of the peptide ligand specifically bind to the opioid receptor and can be radioiodinated. Also provided are methods of making such peptide ligands and OFQR antagonists, and methods of using the ligands for diagnostic and therapeutic uses and for the identification of other naturally-occurring or synthetic opioid receptor ligands.

21 Claims, 14 Drawing Sheets

OTHER PUBLICATIONS

Bunzow et al., "Molecular cloning and tissue distribution of a putative member of the rat opiod gene family that is not a μ, δ or κ opioid receptor type," *FEBS Letters* 347:284–288 (1994).

Coscia et al., "A monoclonal anti–idiotypic antibody to μ and δ opioid receptors," *Molecular Brain Research* 9:299–306 (1991).

Ostresh et al., "'Libraries from libraries': Chemical transformation of combinatorial libraries to extend the range and repertoire of chemical diversity," *PNAS* 91:11138–42 (1994).

Houghten et al., "Generation and use of synthetic peptide combinatorial libraries for basic research and drug discovery," *Nature* 354:84–86 (1991).

Dooley et al., "An all D–Amino Acid Opioid Peptide with Central Analgesic Activity from a Combinatorial Library," *Science* 266:2019–2022 (1994).

Julius, "Home for an orphan endorphin," *Nature* 377:476 (1995).

Meunier et al., "Isolation and structure of the endogenous agonist of opioid receptor–like $ORL_1$ receptor," *Nature* 377:532–535 (1995).

Fukuda et al., "cDNA cloning and regional distribution of a novel member of the opioid receptor family," *FEBS Letters* 343:42–46 (1994).

Chen et al., "Molecular cloning, tissue distribution and chromosomal localization of a novel member of the opioid receptor gene family," *FEBS Letters* 347:279–283 (1994).

Wick et al., "Isolation of a novel cDNA encoding a putative membrane receptor with high homology to the cloned μ, δ, and κ opioid receptors," *Molecular Brain Res.* 27:37–44 (1994).

Hruby et al. *Design of Peptides and Peptideomimetics for Delta and Kappa Opioid Receptor Subtypes;* Dept. Of Chemistry and Pharmacology, Univ. Of Arizona; pp. 123–124; 1994.

Kawasaki et al.; *Design and Synthesis of Highly Potent and Selective Cyclic Dynorphin A Analogues;* J. Med. Chem 33: 1874–1879 (1990).

Kawasaki et al.; *Synthesis, Opioid Binding Affinits, and potencies of Dynorphin A Analogues Substituted in Positions 1, 6, 7, 8 and 10;* Int'l Journal of Peptide & Protein Research; 42 No. 5:411–419 (1993).

Saito et al.; *N23K, A Gene Transiently Up–Regulated During Neural Differentiation, Encodes a Precursor Protein for a Newly Identified Neuropeptide Nociceptin;* Biochemical and Biophysical Research Communications; 217, No. 2:539–545 (Dec. 14,1995).

Reinscheid et al.; *Orphanin FQ: A Neuropeptide That Activates an Opioidlike G Protein —Coupled Receptor,* Science; 270:792–794 (3 Nov., 1995).

```
CCGAGGAGCCATTCCCAGCCGCAGCAGACCCCAATCTAGAGTGAGAGTCATTGCTCAGTCCACTGTGCTCC          71
TGCCTGCCCCGCCTTTCTGCTAAGCATTGGGGTCTATTTTGCGCCACCCAGTTCTGAAGAGGCTGTGTGCCG        142

TTGGAGGAACTGTACTGAGTGGCTTTGCAGGGTGACAGCATGGAGTCCCTCTTCCCTGCTCCATACTGGGAG        214
                              M  E  S  L  F  P  A  P  Y  W  E

GTCCTGTATGGCAGCCACTTTCAAGGAACCTGTCCCTCTAAATGAGACCGTACCCCACCACTGCTCCTC           286
 V  L  Y  G  S  H  F  Q  G  N  L  S  L  L  N  E  T  V  P  H  H  L  L  L
                                  ▲

AATGCTAGTCACACGGCCTTCCTGCCCTTGGACTCAAGGTCACCATCGTGGGGCTCTACTTGGCTGTGTGC        358
 N  A  S  H  S  A  F  L  P │L  G  L  K  V  T  I  V  G  L  Y  L  A  V  C
 ▲                                                                        I

ATCGGGGGCTCCTGGGAACTGCTCGTCATGTATGTCATCCTCAGGCACACCAAGATGAAGACAGCTACC         430
│I  G  G  L  L  G  N  C  L  V  M  Y  V  I  L│R  H  T  K  M  K │T  A  T │

AACATTTACATATTTAATCTGGCACTGGCTGATACCCTGGTCTTGCTAACACTGCCCTTCCAGGGCACAGAC       502
│N  I  Y  I  F  N  L  A  L  A  D  T  L  V  L  L  T  L  P  F  Q  G  T │D
                            II

ATCCTACTGGGCTTCTGGCCATTTGGGAATGCACTGTGCAAGACTGTCATTGCTATCGACTACTACAACATG      574
 I  L  G  F  W  P  F  G  N  A  L  C  K│T  V  I  A  I  D  Y  Y  N  M │
                                                              III

TTTACCAGCACTTTTACTCTGACCCTGCCTATGTGGACCGGCTATGACCGCTATGTGGCCATCTGCCACCCTATCCGTGCC    646
 F  T  S  T  F  T  L  T  A  M  S │V │D  R  Y  V  A  I  C  H  P  I  R  A

CTTGATGTTCGACATCCAGCAAAGCCTGTTAATGTGGCCATATGGGCCCTGGCTTCAGTGGTTGGT              718
 L  D  V  R  T  S  S  K  A  Q │A  V  N  V  A  I  W  A  L  A  S  V  V  G │
                *                                                IV
```

FIG. 1A

```
GTTCCTGTCTTGCCATCATGGGTTCAGCACAAGTGGAAGATGAAGAGATCGAGTGCCTGGTGGAGATCCCTGCC    790
 V  P  V  L  A  I  M  G  S  A  Q  V  E  D  E  E  I  E  C  L  V  E  I  P  A

CCTCAGGACTATTGGGGCCCTGTATTCGCCATCTGCATCTTCCTTTTTCCTTCATCCCTGTCTGATC           862
 P  Q  D  Y  W  G  P  V  F  A  I  C  I  F  L  F  S  F  I  I  P  V  L  I
                                        V

ATCTCCGTCTGCTACAGCCTCATGATTCGACGACTTCGTGGTGTCCGTCTCTTCAGGCTCCCGGGAGAAG        934
 I  S  V  C  Y  S  L  M  I  R  R  L  R  G  V  R  L  L  S  G  S  R  E  K

GACCGAAACCTGCGGCGTATCACTCGACTGGTGCTGGTGGTAGTGGCTGTGTTTGTGGGCTGTTGGACGCCT      1006
 D  R  N  L  R  R  I  T  R  L  V  L  V  V  V  A  V  F  V  G  C  W  T  P

GTGCAGGTGTTTGTCCTGGTTCAAGGACTGGGTGTTCAGCCAGGTAGTGAGACTGCCGTAGCAATCCTGCGC      1078
 V  Q  V  F  V  L  V  Q  G  L  G  V  Q  P  G  S  E  T  A  V  A  I  L  R
                                                      VI

TTCTGCACAGCCCTGGGCTATGTCAACAGTTGTCTCAATCCCATTCTCTATGCTTTCCTGGATGAGAACTTC     1150
 F  C  T  A  L  G  Y  V  N  S  C  L  N  P  I  L  Y  A  F  L  D  D  E  N  F
                VII

AAGGCCTGCTTTAGAAAGTTCTGCTGTGCCTCCTCGCTTCATCCCCGCACCGGGAGATGCAGGTTTCTGATCGTGTGCGG  1222
 K  A  C  F  R  K  F  C  C  A  S  S  L  H  R  E  M  Q  V  S  D  R  V  R
                                                         *

GCGATTGCCAAGGATGTTGGCCTTGGTTGCAAGACTTCTGAGACAGTACCACGGCCCAGCATGACTAGGCGTG     1294
 S  I  A  K  D  V  G  L  G  C  K  T  S  E  T  V  P  R  P  A

GACCTGCCCATGGTGCCTGTCAGCCACAGAGCCCATCCTACACCCAACACGGAGCTCACACAGGTCACTGC       1366
TCTCTAGGTTGACCCTGAACCTTGAGCATCTGAGCCCTTGAATGGCTTTCTTTGGATCAGGATGCTCAGT        1438
CCTAGAGGAAGACC
```

FIG. 1B

Amino acid alignment

```
LC132                         MESLFPAPYWEVL
Rat μ-Opioid Receptor         MDSSTGPGNTSDCSDPLAQASCSPAPGSWLNLS
Mouse δ-Opioid Receptor       MELVPSARAELQSS
Mouse κ-Opioid Receptor       MESPIQIFRGDPGPTCSPSACLLP
```

```
                                           I
                   _____
LC132   YGSHFQGNLSLLNETVPHHLLLNASHSAFLPLGLKVTIVGLYLAVCIGGLLGNCL
μ-OR    HVDGNQSDPCGLNRTGLGGNDSLCPQTGSPSMVTAITIMALYSIVCVVGLFGNFL
δ-OR    PLVNLSDAFPSAFPSAGANASGSPGARSASSLALAIAITALYSAVCAVGLLGNVL
κ-OR    NSSSWFPNWAESDSNGSVGSEDQQLESAHISPAIPVIITAVYSVVFVVGLVGNSL
```

```
                                II
                   _____
LC132   VMYVILRHTKMKTATNIYIFNLALADTLVLLTLPFQGTDILLGFWPFGNALCKTV
μ-OR    VMYVIVRYTKMKTATNIYIFNLALADALATSTLPFQSVNYLMGTWPFFGTILCKIV
δ-OR    VMFGIVRYTKLKTATNIYIFNLALADALATSTLPFQSAKYLMETWPFGELLCKAV
κ-OR    VMFVIIRYTKMKTATNIYIFNLALADALVTTTMPFQSAVYLMNSWPFGDVLCKIV
```

```
                                III                          IV
                   _____    _____
LC132   IAIDYYNMFTSTFTLTAMSVDRYVAICHPIRALDVRTSSKAQAVNVAIWALASVV
μ-OR    ISIDYYNMFTSIFTLCTMSVDRYIAVCHPVKALDFRTPRNAKIVNVCNWILSSAI
δ-OR    LSIDYYNMFTSIFTLTMMSVDRYIAVCHPVKALDFRTPAKAKLINICIWVLASGV
κ-OR    ISIDYYNMFTSIFTLTMMSVDRYIAVCHPVKALDFRTPLKAKIINICIWLLASSV
```

FIG. 2A

```
                                                                              V
LC132  GVPVAIMGSAQ   VEDEEIECLVEIPAP QDYWGPVFA ICIFLFSFIIPVLIISV
μ-OR   GLPVMFMATTK   YRQGSIDCTLTFSHP TWYWENLLK ICVFIFAFIMPILIITV
δ-OR   GVPIMVMAVTQ   PRDFAVVCMLQFPSP SWYWDTVTK ICVFLFAFVVPILIITV
κ-OR   GISAIVLGGTKVREDVDVIECSLQFPDDEYSWWDLFMK ICVFVFAFVIPVLIIIV

VI
LC132  CYSLMIRRLRGVRLLSGS REKDRNLRRIT RLVLVVV AVFVGCWTPVQVFVLVQGL
μ-OR   CYGLMILRLKSVRMLSGS KEKDRNLRRIT RMVLVVV AVF IVCWTPIHIYVIIKAL
δ-OR   CYGLMLLRLRSVRLLSGS KEKDRSLRRIT RMVLVVV GAFVVCWAPIHIFVIVWTL
κ-OR   CYTLMILRLKSVRLLSGS REKDRNLRRIT KLVLVVV AVFIICWTPIHIFILVEAL

VII
LC132  GVQPGSETAVAIL RFCTALGYVNSCLNP ILYAFLDENFKACFRKFCCASSLHRE
μ-OR   ITIPETFQTVSW  HFCIALGYTNSCLNP VLYAFLDENFKRCFREFCIPTSSTIE
δ-OR   VDINRRDPLVVAALHLCIALGY ANS SLNPVLYAFLDENFKRCFRQLCRTPCGRQE
κ-OR   GSTSHSTAALSSY YFCIALGYTNS SLNPVLYAFLDENFKRCFRDFCFPIKMRME

LC132  MQVSDRVRSIAKDVGLGCKTSETVPRPA 367
μ-OR   QQNSTRVRQNTREHPSTANTVDRTNHQLENLEAETAPLP 398
δ-OR   PGSLRRPRQATTRERVTACTPSDGPGGAAA 372
κ-OR   RQSTNRVRNTVQDPASMRDVGGMNKPV 380
```

FIG. 2B

3H-METHADONE BINDING TO COS-7 MEMBRANES

3H-METHADONE BINDING TO LC132 IN COS-7 MEMBRANES

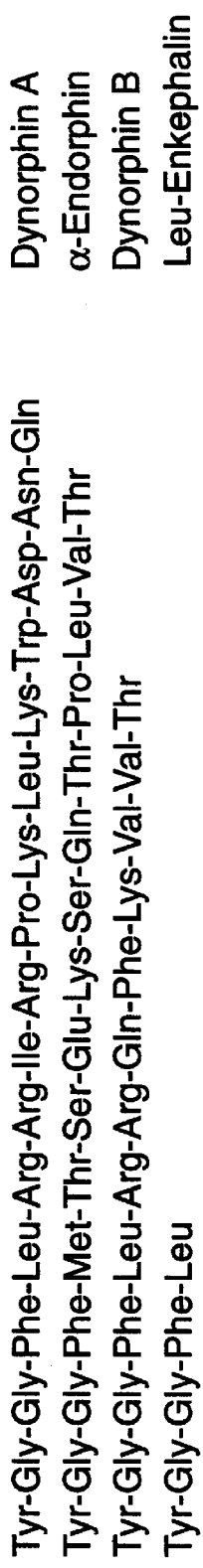
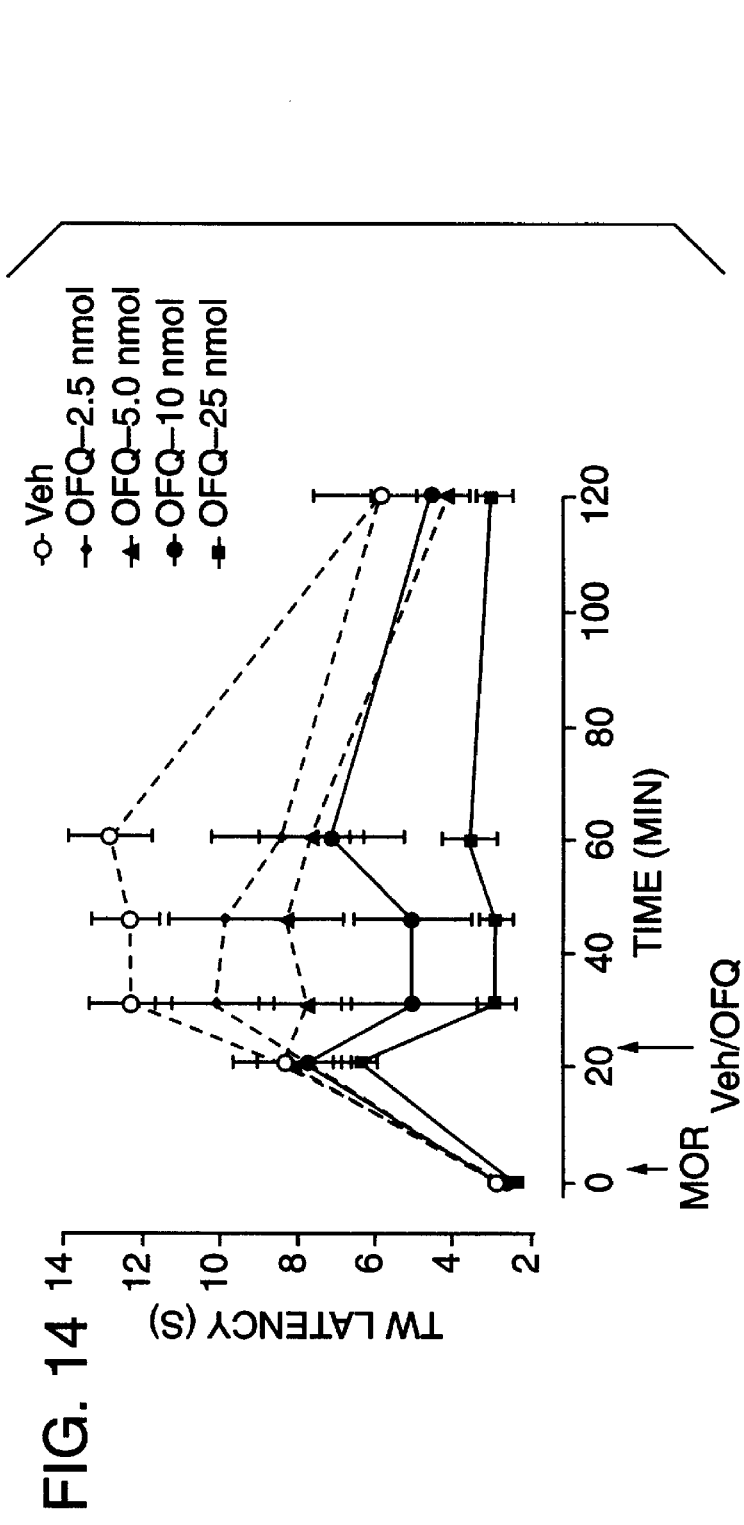
FIG. 7
Tyr-Gly-Gly-Phe-Leu-Arg-Arg-Ile-Arg-Pro-Lys-Leu-Lys-Trp-Asp-Asn-Gln
Tyr-Gly-Gly-Phe-Met-Thr-Ser-Glu-Lys-Ser-Gln-Thr-Pro-Leu-Val-Thr
Tyr-Gly-Gly-Phe-Leu-Arg-Arg-Gln-Phe-Lys-Val-Val-Thr
Tyr-Gly-Gly-Phe-Leu
Dynorphin A
α-Endorphin
Dynorphin B
Leu-Enkephalin
FIG. 14

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA (genomic)

( x i ) SEQUENCE DESCRIPTION: SEQ ID NO:1:

```
ATGAATTCAC NRTSATGAGY GTSGACHGHT A                                    31
```

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA (genomic)

( x i ) SEQUENCE DESCRIPTION: SEQ ID NO:2:

```
TTGTCGACRT ARRAGRAYNG GRTT                                            24
```

( 2 ) INFORMATION FOR SEQ ID NO:3:

( i ) SEQUENCE CHARACTERISTICS:
        ( A ) LENGTH: 1452 base pairs
        ( B ) TYPE: nucleic acid
        ( C ) STRANDEDNESS: single
        ( D ) TOPOLOGY: linear ( i i ) MOLECULE TYPE:
        ( A ) DESCRIPTION: cDNA ( i x ) FEATURE:
        ( A ) NAME/KEY: 5'UTR
        ( B ) LOCATION: 1..181

( i x ) FEATURE:
        ( A ) NAME/KEY: CDS
        ( B ) LOCATION: 182..1282

( i x ) FEATURE:
        ( A ) NAME/KEY: 3'UTR
        ( B ) LOCATION: 1283..1452

( x i ) SEQUENCE DESCRIPTION: SEQ ID NO:3:

```
CCGAGGAGCC ATTCCCAGCC GCAGCAGACC CCAATCTAGA GTGAGAGTCA TTGCTCAGTC        60

CACTGTGCTC CTGCCTGCCC GCCTTTCTGC TAAGCATTGG GGTCTATTTT GCGCCCAGCT       120

TCTGAAGAGG CTGTGTGTGC CGTTGGAGGA ACTGTACTGA GTGGCTTTGC AGGGTGACAG       180

C ATG GAG TCC CTC TTT CCT GCT CCA TAC TGG GAG GTC TTG CAT GGC           226
  Met Glu Ser Leu Phe Pro Ala Pro Tyr Trp Glu Val Leu His Gly
  1               5                   10                  15

AGC CAC TTT CAA GGG AAC CTG TCC CTC CTA AAT GAG ACC GTA CCC CAC         274
Ser His Phe Gln Gly Asn Leu Ser Leu Leu Asn Glu Thr Val Pro His
                20                  25                  30

CAC CTG CTC CTC AAT GCT AGT CAC AGC GCC TTC TGC CCC TTG GGA CTC         322
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| His | Leu | Leu | Leu | Asn | Ala | Ser | His | Ser | Ala | Phe | Leu | Pro | Leu | Gly | Leu |      |
|     |     |     | 35  |     |     |     | 40  |     |     |     |     | 45  |     |     |     |      |
| AAG | GTC | ACC | ATC | GTG | GGG | CTC | ATC | TTG | GCT | GTG | TGC | ATC | GGG | GGG | CTC | 370  |
| Lys | Val | Thr | Ile | Val | Gly | Leu | Ile | Leu | Ala | Val | Cys | Ile | Gly | Gly | Leu |      |
|     |     | 50  |     |     |     | 55  |     |     |     |     | 60  |     |     |     |     |      |
| CTG | GGG | AAC | TGC | CTC | GTC | ATG | TAT | GTC | ATC | CTC | AGG | ACA | CCC | AAG | ATG | 418  |
| Leu | Gly | Asn | Cys | Leu | Val | Met | Tyr | Val | Ile | Leu | Arg | Thr | Pro | Lys | Met |      |
|     | 65  |     |     |     | 70  |     |     |     |     | 75  |     |     |     |     |     |      |
| AAG | ACA | GCT | ACC | AAC | ATT | TAC | ATA | TTT | AAT | CTG | GCA | CTG | GCT | GAT | ACC | 466  |
| Lys | Thr | Ala | Thr | Asn | Ile | Tyr | Ile | Phe | Asn | Leu | Ala | Leu | Ala | Asp | Thr |      |
| 80  |     |     |     |     | 85  |     |     |     |     | 90  |     |     |     |     | 95  |      |
| CTG | GTC | TTG | CTA | ACA | CTG | CCC | TTC | CAG | GGC | ACA | GAC | ATC | CTA | CTG | GGC | 514  |
| Leu | Val | Leu | Leu | Thr | Leu | Pro | Phe | Gln | Gly | Thr | Asp | Ile | Leu | Leu | Gly |      |
|     |     |     |     | 100 |     |     |     |     | 105 |     |     |     |     | 110 |     |      |
| TTC | TGG | CCA | TTT | GGG | AAA | GCA | CTC | TGC | AAG | ACT | GTC | ATT | GCT | ATC | GAC | 562  |
| Phe | Trp | Pro | Phe | Gly | Lys | Ala | Leu | Cys | Lys | Thr | Val | Ile | Ala | Ile | Asp |      |
|     |     |     | 115 |     |     |     |     | 120 |     |     |     |     | 125 |     |     |      |
| TAC | TAC | AAC | ATG | TTT | ACC | AGC | ACT | TTT | ACT | CTG | ACC | GCC | ATG | AGC | GTA | 610  |
| Tyr | Tyr | Asn | Met | Phe | Thr | Ser | Thr | Phe | Thr | Leu | Thr | Ala | Met | Ser | Val |      |
|     |     | 130 |     |     |     |     | 135 |     |     |     |     | 140 |     |     |     |      |
| GAC | CGC | TAT | GTG | GCT | ATC | TGC | CAC | CCT | ATC | CGT | GCC | CTT | GAT | GTT | CGG | 658  |
| Asp | Arg | Tyr | Val | Ala | Ile | Cys | His | Pro | Ile | Arg | Ala | Leu | Asp | Val | Arg |      |
|     | 145 |     |     |     |     | 150 |     |     |     |     | 155 |     |     |     |     |      |
| ACA | TCC | AGC | AAA | GCC | CAG | GCT | GTT | AAT | GTG | GCC | ATA | TGG | GCC | CTG | GCT | 706  |
| Thr | Ser | Ser | Lys | Ala | Gln | Ala | Val | Asn | Val | Ala | Ile | Trp | Ala | Leu | Ala |      |
| 160 |     |     |     |     | 165 |     |     |     |     | 170 |     |     |     |     | 175 |      |
| TCA | GTG | GTT | GGT | GTT | CCT | GTT | GCC | ATC | ATG | GGT | TCA | GCA | CAA | GTG | GAA | 754  |
| Ser | Val | Val | Gly | Val | Pro | Val | Ala | Ile | Met | Gly | Ser | Ala | Gln | Val | Glu |      |
|     |     |     |     |     | 180 |     |     |     | 185 |     |     |     |     | 190 |     |      |
| GAT | GAA | GAG | ATC | GAG | TGC | CTG | GTG | GAG | ATC | CCT | GCC | CCT | CAG | GAC | TAT | 802  |
| Asp | Glu | Glu | Ile | Glu | Cys | Leu | Val | Glu | Ile | Pro | Ala | Pro | Gln | Asp | Tyr |      |
|     |     |     | 195 |     |     |     |     | 200 |     |     |     |     | 205 |     |     |      |
| TGG | GGC | CCT | GTA | TTC | GCC | ATC | TGC | ATC | TTC | CTT | TTT | TCC | TTC | ATC | ATC | 850  |
| Trp | Gly | Pro | Val | Phe | Ala | Ile | Cys | Ile | Phe | Leu | Phe | Ser | Phe | Ile | Ile |      |
|     |     | 210 |     |     |     |     | 215 |     |     |     |     | 220 |     |     |     |      |
| CCT | GTG | CTG | ATC | ATC | TCT | GTC | TGC | TAC | AGC | CTC | ATG | ATT | CGA | CGA | CTT | 898  |
| Pro | Val | Leu | Ile | Ile | Ser | Val | Cys | Tyr | Ser | Leu | Met | Ile | Arg | Arg | Leu |      |
|     | 225 |     |     |     |     | 230 |     |     |     |     | 235 |     |     |     |     |      |
| CGT | GGT | GTC | CGT | CTG | CTT | TCA | GGC | TCC | CGG | GAG | AAG | GAC | CGA | AAC | CTG | 946  |
| Arg | Gly | Val | Arg | Leu | Leu | Ser | Gly | Ser | Arg | Glu | Lys | Asp | Arg | Asn | Leu |      |
| 240 |     |     |     |     | 245 |     |     |     |     | 250 |     |     |     |     | 255 |      |
| CGG | CGT | ATC | ACT | CGA | CTG | GTG | CTG | GTA | GTG | GTG | GCT | GTG | TTT | GTG | GGC | 994  |
| Arg | Arg | Ile | Thr | Arg | Leu | Val | Leu | Val | Val | Val | Ala | Val | Phe | Val | Gly |      |
|     |     |     |     | 260 |     |     |     |     | 265 |     |     |     |     | 270 |     |      |
| TGC | TGG | ACG | CCT | GTG | CAG | GTG | TTT | GTC | CTG | GTT | CAA | GGA | CTG | GGT | GTT | 1042 |
| Cys | Trp | Thr | Pro | Val | Gln | Val | Phe | Val | Leu | Val | Gln | Gly | Leu | Gly | Val |      |
|     |     |     | 275 |     |     |     |     | 280 |     |     |     |     | 285 |     |     |      |
| CAG | CCA | GGT | AGT | GAG | ACT | GCA | GTT | GCC | ATC | CTG | CGC | TTC | TGC | ACA | GCC | 1090 |
| Gln | Pro | Gly | Ser | Glu | Thr | Ala | Val | Ala | Ile | Leu | Arg | Phe | Cys | Thr | Ala |      |
|     |     | 290 |     |     |     |     | 295 |     |     |     |     | 300 |     |     |     |      |
| CTG | GGC | TAT | GTC | AAC | AGT | TGT | CTC | AAT | CCC | ATT | CTC | TAT | GCT | TTC | CTG | 1138 |
| Leu | Gly | Tyr | Val | Asn | Ser | Cys | Leu | Asn | Pro | Ile | Leu | Tyr | Ala | Phe | Leu |      |
|     |     | 305 |     |     |     |     | 310 |     |     |     |     | 315 |     |     |     |      |
| GAT | GAG | AAC | TTC | AAG | GCC | TGC | TTT | AGA | AAG | TTC | TGC | TGT | GCT | TCA | TCC | 1186 |
| Asp | Glu | Asn | Phe | Lys | Ala | Cys | Phe | Arg | Lys | Phe | Cys | Cys | Ala | Ser | Ser |      |
| 320 |     |     |     |     | 325 |     |     |     |     | 330 |     |     |     |     | 335 |      |
| CTG | CAC | CGG | GAG | ATG | CAG | GTT | TCT | GAT | CGT | GTG | CGG | ACG | ATT | GCC | AAG | 1234 |
| Leu | His | Arg | Glu | Met | Gln | Val | Ser | Asp | Arg | Val | Arg | Thr | Ile | Ala | Lys |      |
|     |     |     |     | 340 |     |     |     |     | 345 |     |     |     |     | 350 |     |      |
| GAT | GTT | GGC | CTT | GGT | TGC | AAG | ACT | TCT | GAG | ACA | GTA | CCA | CGG | CCA | GCA | 1282 |

-continued

| Asp | Val | Gly | Leu | Gly | Cys | Lys | Thr | Ser | Glu | Thr | Val | Pro | Arg | Pro | Ala |
|---|---|---|---|---|---|---|---|---|---|---|---|---|---|---|---|
| | | | 355 | | | | 360 | | | | | 365 | | | |

TGACTAGGCG TGGACCTGCC CATGGTGCCT GTCAGCCCAC AGAGCCCATC CTACACCCAA 1342

CACGGAGCTC ACACAGGTCA CTGCTCTCTA GGTTGACCCT GAACCTTGAG CATCTGGAGC 1402

CTTGAATGGC TTTTCTTTTG GATCAGGATG CTCAGTCCTA GAGGAAGACC 1452

( 2 ) INFORMATION FOR SEQ ID NO: 4:

( i ) SEQUENCE CHARACTERISTICS:
        ( A ) LENGTH: 367 amino acids
        ( B ) TYPE: amino acid
        ( D ) TOPOLOGY: linear ( i i ) MOLECULE TYPE:
        ( A ) DESCRIPTION: protein ( x i ) SEQUENCE DESCRIPTION: SEQ ID NO:4:

| Met | Glu | Ser | Leu | Phe | Pro | Ala | Pro | Tyr | Trp | Glu | Val | Leu | His | Gly | Ser |
|---|---|---|---|---|---|---|---|---|---|---|---|---|---|---|---|
| 1 | | | | 5 | | | | | 10 | | | | | 15 | |

| His | Phe | Gln | Gly | Asn | Leu | Ser | Leu | Leu | Asn | Glu | Thr | Val | Pro | His | His |
|---|---|---|---|---|---|---|---|---|---|---|---|---|---|---|---|
| | | | 20 | | | | | 25 | | | | | 30 | | |

| Leu | Leu | Leu | Asn | Ala | Ser | His | Ser | Ala | Phe | Leu | Pro | Leu | Gly | Leu | Lys |
|---|---|---|---|---|---|---|---|---|---|---|---|---|---|---|---|
| | | 35 | | | | | 40 | | | | | 45 | | | |

| Val | Thr | Ile | Val | Gly | Leu | Ile | Leu | Ala | Val | Cys | Ile | Gly | Gly | Leu | Leu |
|---|---|---|---|---|---|---|---|---|---|---|---|---|---|---|---|
| | 50 | | | | | 55 | | | | | 60 | | | | |

| Gly | Asn | Cys | Leu | Val | Met | Tyr | Val | Ile | Leu | Arg | Thr | Pro | Lys | Met | Lys |
|---|---|---|---|---|---|---|---|---|---|---|---|---|---|---|---|
| 65 | | | | | 70 | | | | | 75 | | | | | 80 |

| Thr | Ala | Thr | Asn | Ile | Tyr | Ile | Phe | Asn | Leu | Ala | Leu | Ala | Asp | Thr | Leu |
|---|---|---|---|---|---|---|---|---|---|---|---|---|---|---|---|
| | | | | 85 | | | | | 90 | | | | | 95 | |

| Val | Leu | Leu | Thr | Leu | Pro | Phe | Gln | Gly | Thr | Asp | Ile | Leu | Leu | Gly | Phe |
|---|---|---|---|---|---|---|---|---|---|---|---|---|---|---|---|
| | | | 100 | | | | | 105 | | | | | 110 | | |

| Trp | Pro | Phe | Gly | Lys | Ala | Leu | Cys | Lys | Thr | Val | Ile | Ala | Ile | Asp | Tyr |
|---|---|---|---|---|---|---|---|---|---|---|---|---|---|---|---|
| | | 115 | | | | | 120 | | | | | 125 | | | |

| Tyr | Asn | Met | Phe | Thr | Ser | Thr | Phe | Thr | Leu | Thr | Ala | Met | Ser | Val | Asp |
|---|---|---|---|---|---|---|---|---|---|---|---|---|---|---|---|
| | 130 | | | | | 135 | | | | | 140 | | | | |

| Arg | Tyr | Val | Ala | Ile | Cys | His | Pro | Ile | Arg | Ala | Leu | Asp | Val | Arg | Thr |
|---|---|---|---|---|---|---|---|---|---|---|---|---|---|---|---|
| 145 | | | | | 150 | | | | | 155 | | | | | 160 |

| Ser | Ser | Lys | Ala | Gln | Ala | Val | Asn | Val | Ala | Ile | Trp | Ala | Leu | Ala | Ser |
|---|---|---|---|---|---|---|---|---|---|---|---|---|---|---|---|
| | | | | 165 | | | | | 170 | | | | | 175 | |

| Val | Val | Gly | Val | Pro | Val | Ala | Ile | Met | Gly | Ser | Ala | Gln | Val | Glu | Asp |
|---|---|---|---|---|---|---|---|---|---|---|---|---|---|---|---|
| | | | 180 | | | | | 185 | | | | | 190 | | |

| Glu | Glu | Ile | Glu | Cys | Leu | Val | Glu | Ile | Pro | Ala | Pro | Gln | Asp | Tyr | Trp |
|---|---|---|---|---|---|---|---|---|---|---|---|---|---|---|---|
| | | | 195 | | | | | 200 | | | | | 205 | | |

| Gly | Pro | Val | Phe | Ala | Ile | Cys | Ile | Phe | Leu | Phe | Ser | Phe | Ile | Ile | Pro |
|---|---|---|---|---|---|---|---|---|---|---|---|---|---|---|---|
| | 210 | | | | | 215 | | | | | 220 | | | | |

| Val | Leu | Ile | Ile | Ser | Val | Cys | Tyr | Ser | Leu | Met | Ile | Arg | Arg | Leu | Arg |
|---|---|---|---|---|---|---|---|---|---|---|---|---|---|---|---|
| 225 | | | | | 230 | | | | | 235 | | | | | 240 |

| Gly | Val | Arg | Leu | Leu | Ser | Gly | Ser | Arg | Glu | Lys | Asp | Arg | Asn | Leu | Arg |
|---|---|---|---|---|---|---|---|---|---|---|---|---|---|---|---|
| | | | | 245 | | | | | 250 | | | | | 255 | |

| Arg | Ile | Thr | Arg | Leu | Val | Leu | Val | Val | Val | Ala | Val | Phe | Val | Gly | Cys |
|---|---|---|---|---|---|---|---|---|---|---|---|---|---|---|---|
| | | | 260 | | | | | 265 | | | | | 270 | | |

| Trp | Thr | Pro | Val | Gln | Val | Phe | Val | Leu | Val | Gln | Gly | Leu | Gly | Val | Gln |
|---|---|---|---|---|---|---|---|---|---|---|---|---|---|---|---|
| | | 275 | | | | | 280 | | | | | 285 | | | |

| Pro | Gly | Ser | Glu | Thr | Ala | Val | Ala | Ile | Leu | Arg | Phe | Cys | Thr | Ala | Leu |
|---|---|---|---|---|---|---|---|---|---|---|---|---|---|---|---|
| | 290 | | | | | 295 | | | | | 300 | | | | |

| Gly | Tyr | Val | Asn | Ser | Cys | Leu | Asn | Pro | Ile | Leu | Tyr | Ala | Phe | Leu | Asp |
|---|---|---|---|---|---|---|---|---|---|---|---|---|---|---|---|

```
3 0 5                       3 1 0                       3 1 5                       3 2 0
Glu  Asn  Phe  Lys  Ala  Cys  Phe  Arg  Lys  Phe  Cys  Cys  Ala  Ser  Ser  Leu
                    3 2 5                       3 3 0                       3 3 5

His  Arg  Glu  Met  Gln  Val  Ser  Asp  Arg  Val  Arg  Thr  Ile  Ala  Lys  Asp
               3 4 0                       3 4 5                       3 5 0

Val  Gly  Leu  Gly  Cys  Lys  Thr  Ser  Glu  Thr  Val  Pro  Arg  Pro  Ala
               3 5 5                       3 6 0                       3 6 5
```

( 2 ) INFORMATION FOR SEQ ID NO: 5:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE:
        ( A ) DESCRIPTION: peptide ( x i ) SEQUENCE DESCRIPTION: SEQ ID NO:5:

```
Phe  Gly  Gly  Phe  Thr  Gly  Ala  Arg  Lys  Ser  Ala  Arg  Lys  Leu  Ala  Asn
1                   5                        1 0                       1 5
Gln
```

( 2 ) INFORMATION FOR SEQ ID NO: 6:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE:
        ( A ) DESCRIPTION: peptide ( x i ) SEQUENCE DESCRIPTION: SEQ ID NO:6:

```
Phe  Gly  Gly  Phe  Thr  Gly  Ala  Arg  Lys  Ser  Ala  Arg  Lys  Tyr  Ala  Asn
1                   5                        1 0                       1 5
Gln
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 7:

```
Tyr  Gly  Gly  Phe  Leu  Arg  Arg  Ile  Arg  Pro  Lys  Leu  Lys  Trp  Asp  Asn  Gln
1                   5                        1 0                       1 5
```

( 2 ) INFORMATION FOR SEQ ID NO: 8:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 8:

```
Tyr  Gly  Gly  Phe  Met  Thr  Ser  Glu  Lys  Ser  Gln  Thr  Pro  Leu  Val  Thr
1                   5                        1 0                       1 5
```

( 2 ) INFORMATION FOR SEQ ID NO: 9:

-continued

```
(i) SEQUENCE CHARACTERISTICS:
    (A) LENGTH: 13 amino acids
    (B) TYPE: amino acid
    (D) TOPOLOGY: linear (ii) MOLECULE TYPE: peptide (xi) SEQUENCE DESCRIPTION: SEQ ID NO: 9:

Tyr  Gly  Gly  Phe  Leu  Arg  Arg  Gln  Phe  Lys  Val  Val  Thr
1                  5                        10

(2) INFORMATION FOR SEQ ID NO: 10:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 10:

Tyr  Gly  Gly  Phe  Leu
1                  5

(2) INFORMATION FOR SEQ ID NO: 11:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 11:

Xaa  Phe  Gly  Gly  Phe  Xaa
1                  5
```

OPIOID ANTAGONISTS AND METHODS OF THEIR USE

This is a continuation in part of pending U.S. application Ser. No. 08/514,451 filing date Aug. 11, 1995 entitled A NOVEL MAMMALIAN OPIOID RECEPTOR LIGAND.

This invention was made at least in part with government support under National Institutes of Health grant RO1 MH48991. The government may have certain rights to this invention.

BACKGROUND OF THE INVENTION

1. Field of the Invention

This invention relates to receptors from mammalian species and ligands specific for such receptors, which are active in the antagonism of opioid action. Specifically, the invention relates to the isolation of an endogenous peptide ligand specific for a novel mammalian receptor, the recognition of its anti-opioid properties, and use of the ligand for reversing physiologic effects of opiates such as morphine. The invention also relates to the construction of analogues, derivatives and peptide mimetics of this endogenous mammalian receptor ligand, and their use as opiate antagonists. Specifically provided is a mammalian hypothalamus-derived endogenous opioid receptor ligand, synthetic embodiments and analogues thereof, and methods of making and using such ligands.

2. Background of the Invention

The use (and abuse) of opiates, such as opium and morphine, have been known since antiquity (reviewed in Brownstein, 1993, Proc. Natl. Acad. Sci. USA 90: 5391–5393). Since the nineteenth century, chemical characterization and synthesis of many morphine analogues have been achieved in an effort to discover a compound having the analgesic effects of morphine but lacking its addictive potential. These efforts have heretofore been unsuccessful.

The biology behind the reasons for the analgesic and addictive properties of morphine and morphine-like compounds was first elucidated by the discovery of endogenous morphine-like compounds termed enkephalins (see DiChara & North, 1992, Trends in Pharmacol. Sci. 13: 185–193 for review). Accompanying this finding of an endogenous opioid was the biochemical evidence for a family of related but distinct opiate receptors, each of which displays a unique pharmacological profile of response to opiate agonists and antagonists (see McKnight & Rees, 1991, Neurotransmissions 7: 1–6 for review). To date, four distinct opiate receptors have been described by their pharmacological profiles and anatomical distribution: these comprise the $\mu$, $\delta$, $\kappa$, and $\sigma$ receptors (the $\sigma$ receptor has been determined to be a non-opioid receptor displaying cross-reactivity with some opioid agonists).

Thus, mammalian opioid receptors are known in the art, and some of these proteins have been isolated biochemically and their corresponding genes have been recently cloned using genetic engineering means.

Kieffer et al., 1992, Proc. Natl. Acad. Sci. USA 89: 12048–12052 disclosed the isolation of a cDNA copy of the mouse $\delta$-opioid receptor by expression cloning.

Evans et al., 1992, Science 258: 1952–1955 disclosed the isolation of a cDNA copy of the mouse $\delta$-opioid receptor by expression cloning.

Chen et al., 1993, Molec. Pharmacol. 44: 8–12 disclosed the isolation of a cDNA copy of the rat $\mu$-opioid receptor.

Yasuda et al., 1993, Proc. Natl. Acad. Sci. USA 90: 6736–6740 disclosed the isolation of a cDNA copy of each of the mouse $\kappa$- and $\delta$-opioid receptor.

Bzdega et al., 1993, Proc. Natl. Acad. Sci. USA 90: 9305–9309 disclose the isolation and chromosomal location of the $\delta$-opioid receptor in the mouse.

The present inventors have cloned, expressed and functionally characterized a novel mammalian receptor gene, disclosed in co-owned and co-pending U.S. patent application Ser. No. 08/149,093, filed Nov. 8, 1993, which is hereby incorporated by reference in its entirety. Specifically disclosed therein are nucleic acids encoding the novel mammalian receptor gene, recombinant expression constructs comprising this receptor gene, cells containing such constructs and expressing the novel receptor gene, and methods for making and using such nucleic acids, as well as constructs and cells for opioid detection and novel drug screening. The nucleic acid sequence of the gene and the deduced amino acid sequence of the cognate receptor protein were also disclosed in this prior application.

The receptor gene was previously referred to in the co-pending case as an MSOR (methadone specific opioid receptor) gene because the receptor bound methadone with a high affinity. Such high affinity constitutes a specificity for methadone, although this term is not intended to imply that only methadone binds to the receptor. Indeed, as shown herein, an endogenous ligand of the present invention binds to the same receptor with startlingly high affinity (producing a physiologic response when administered in a picomole or nanomole dose i.c.v.). Now that the endogenous ligand has been discovered, and disclosed in co-owned and co-pending U.S. patent application Ser. No. 08/514,451 filed Aug. 11, 1995, the MSOR terminology is no longer needed. The ligand has been named orphanin FQ (OFQ) from the initial and terminal amino acids of the disclosed sequence (F for phenylalanine and Q for glutamine). Hence the receptor will now be referred to as the orphanin FQ receptor (OFQR), which is an anti-opioid receptor (AOR).

A great advantage in efforts for developing novel psychotropic drugs which exert their activity (analgesic and otherwise) via binding to mammalian opioid or anti-opioid receptors would be to identify the endogenous ligand(s) which bind to such receptors. Certain such opioid ligands have been isolated in the prior art, including the peptides comprising the endorphins and enkephalins (see Jaffe and Martin, 1990, "Opioid Analgesics and Antagonists", in Goodman and Gilman, eds., *The Pharmacological Basis of Therapeutics,* 7th ed. (Pergammon Press, Inc.: New York), Chapter 21, p. 491–531).

Although opiates are powerful therapeutic agents, their therapeutic index is sufficiently low to cause many problems in their clinical use. Such problems include stupor, respiratory compromise, or profound analgesia that may be undesired (and mask symptoms of an acute surgical emergency, such as appendicitis). Physical dependence on morphine or other opiates can also develop, and may be difficult for a clinician to diagnose. It has been recognized that administration of an antagonist to reverse opiate effects is clinically useful in these circumstances, either for reducing physiologic effects of the opiate (undesired analgesia or apnea), or precipitating a withdrawal syndrome to demonstrate addiction.

In spite of the importance of opioid antagonists, progress has only slowly been made in developing additional members of this class of drugs. The best known such antagonist is naloxone, an organically synthesized molecule that resembles oxymorphone and is a competitive antagonist at $\mu$, $\delta$, $\kappa$ and $\sigma$ opioid receptors. Naltrexone appears to be another relatively pure antagonist, but with higher oral efficacy and a longer duration of action. These drugs are believed to interact with and competitively bind to the opioid receptors to exert their antagonistic action. They reverse signs of opiate intoxication such as apnea and stupor, and they can also stimulate a withdrawal syndrome in drug dependent subjects characterized by anxiety, chills, abdominal cramping, tachycardia lacrimation and sweating. The search for additional opioid antagonists has continued, because of a clinical need for such drugs. Endogenous antagonists have been particularly pursued because of their predicted potency, and the invaluable information they would provide about the body's physiologic pathways for developing tolerance and addiction. In spite of these advantages, such endogenous anti-opioids have eluded investigators for years.

SUMMARY OF THE INVENTION

The present invention takes advantage of the discovery that an anti-opioid biological system physiologically counteracts or antagonizes the actions mediated by the binding of opioids to opioid receptors. The OFQ anti-opioid receptor is the same receptor (MSOR) disclosed in the commonly assigned U.S. patent application Ser. No. 08/149,093. The ligand of the present invention is the ligand disclosed in commonly assigned U.S. patent application Ser. No. 08/514,451. The method of treatment of the present application was made possible by the present inventors' recognition that the receptor is an anti-opioid receptor that, when bound to a ligand of the present invention, antagonizes the physiologic effects of an opioid.

This invention provides small, readily-produced peptides that are ligands for a novel mammalian anti-opioid receptor protein having the amino acid sequence identified as SEQ ID Nos.: 5 and 6. Peptides of the invention are characterized as having the amino acid sequence identified as SEQ ID Nos.: 5 and 6 or a subsequence thereof, amino acid sequence variants of the sequence or subsequence, as well as analogues and derivatives thereof, that are ligands for the mammalian opioid receptor protein having the amino acid sequence identified as SEQ ID Nos.: 5 and 6, as well as analogues and derivatives thereof.

The method of the present invention antagonizes a physiological effect (such as analgesia or hypothermia) of an opioid (such as morphine or heroin) in an animal (such as a rodent or a human). The method includes administering to the animal a pharmaceutically effective amount of the peptide, which specifically binds to a receptor encoded by the DNA molecule set forth in SEQ. ID. No. 3. The peptide is preferably an heptadecapeptide having an aminoterminal FGGF motif, and the peptide does not bind with high specificity to mu, delta, or kappa opioid receptors. It antagonizes physiologic opioid effects (such as analgesia or hypothermia) without increasing nociceptive sensitivity beyond the baseline sensitivity of the animal to painful stimuli in the absence of the exogenous opioid or stress induced analgesia. Stress induced analgesia is a normal physiologic mechanism, believed to be mediated by endogenous opioids, for reducing pain perception in response to stressful environmental stimuli.

A pharmaceutically effective amount of the peptide is an amount sufficient to subjectively or objectively diminish the effects of the opiate. An example would be an amount sufficient to reverse the degree of analgesia to painful stimuli induced by an opioid, or an amount sufficient to raise body temperature of an animal experiencing opiate induced hypothermia. In some of the described embodiments, this amount would be a picomolar or nanomolar icv dose. For example, a pharmaceutically effective dose in a mouse would be a 50 picomole to 10 nanomole intracranial ventricular (icv) dose, in 2 $\mu$l vehicle. The present invention may be administered by many routes, including intravenously (iv), subcutaneously (sc), or intrathecally (it). Given the marked anti-opioid potency of the peptide, relatively low doses of the peptide could even be given iv. Human doses given icv and intrathecally would be expected to be 1–10 nanomoles in a 2 microliter volume.

In yet other embodiments, the peptide may be an analogue, derivative or mimetic of the peptides. An analogue is a peptide having the same anti-opioid activity as the disclosed peptides, but differing in primary amino acid sequence. The variations in the primary amino acid sequence could be made using the techniques described in this specification, and known in the art. A mimetic of the peptide is a molecule, either a peptide or other biopharmaceutical (such as an organically synthesized compound) that specifically binds to a receptor encoded by SEQ. ID. No. 3 and antagonizes a physiological effect of an opioid in an animal.

In other embodiments of the invention, the method includes administering to the animal a second anti-opioid antagonist, wherein the second anti-opioid antagonist and anti-opioid peptide are administered in a sufficient amount in combination to antagonize physiological effects of the opioid. The first and second antagonists may be given either in series or administered together in a mixture. For example, the anti-opioid peptide can be administered in a vehicle (such as isotonic saline solution) in admixture with naloxone (at a pharmaceutically effective dose of 1 mg/kg body weight of the animal). Alternatively, the anti-opioid peptide can be administered in combination with other anti-opioid peptides (such as analogues of the peptide of the present invention, or other endogenous or synthetic peptides that have an anti-opioid activity).

The peptides of the invention include linear and cyclized peptides, and synthetic analogues and variants thereof. Certain embodiments of such variants include substitution variants, wherein an amino acid residue at one or more positions in the peptide is replaced with a different amino acid residue (including atypical amino acid residues) from that found in the corresponding position of the amino acid sequence of the parent peptide of the invention. Certain other embodiments of peptide variants of the invention include addition variants, wherein such variant peptides may include up to about a total of 10 additional amino acids, covalently linked to either the amino-terminal or carboxyl-terminal extent, or both, of the parent peptide of the present invention. Such additional amino acids may also include atypical amino acids. Linear and cyclized embodiments of the amino acid substitution and addition variant peptides are also provided as peptides of the invention. In addition, peptides of the invention may be provided as fusion proteins with other functional targeting agents, such as immunoglobulin fragments. Derivatives of the peptides of the invention also include modifications of the amino- and carboxyl-termini and amino acid side chain chemical groups such as amines, carboxylic acids, alkyl and phenyl groups.

In a first aspect, the invention provides peptides of the formula:

$(Xaa)_n$-Phe-Gly-Gly-Phe-$(A^1)$-$(A^2)$-$(A^3)$-$(A^4)$-$(A^5)$-$(A^6)$-$(A^7)$-$(A^8)$-$(A^9)$-$(A^{10})$-$(A^{11})$-$(A^{12})$-Gln-$(Xaa)_m$ (SEQ. ID. No. 11)

wherein $A^1$ is Thr, Leu or Met;

$A^2$ is Gly, Arg or Thr;

$A^3$ is Ala, Arg or Ser;

$A^4$ is Arg, Ile, Glu or Gln;

$A^5$ is Lys, Arg or Phe;

$A^6$ is Ser, Pro or Lys;

$A^7$ is Ala, Lys, Gln or Val;

$A^8$ is Arg, Leu, Thr or Val;

$A^9$ is Lys, Pro or Thr;

$A^{10}$ is Tyr, Leu or Trp;

$A^{11}$ is Ala, Asp or Val;

$A^{12}$ is Asn, or Thr;

(Xaa) is any amino acid;

n and m are integers wherein n+m is no more than 82, preferably no more than 20, or even no more than 10; and the amino acids are each individually in either the D or L stereochemical configuration and the peptide specifically binds to a mammalian opioid receptor having an amino acid sequence identified by SEQ ID No. 4.

In a preferred embodiment, the peptide has the formula:

Phe-Gly-Gly-Phe-Thr-Gly-Ala-Arg-Lys-Ser-Ala-Arg-Lys-Leu-Ala-Asn-Gln (SEQ ID No.: 5).

In an another preferred embodiment, the peptide has the formula:

Phe-Gly-Gly-Phe-Thr-Gly-Ala-Arg-Lys-Ser-Ala-Arg-Lys-Tyr-Ala-Asn-Gln (SEQ ID No.: 6).

Naturally-occurring embodiments of the peptides, purified using well-established techniques from the cells or tissues producing the peptide, and synthetic embodiments, are within the scope of the invention.

In other embodiments the peptides are of the general formula:

$(Xaa)_n$-Phe-Gly-Gly-Phe-$(A^1)$-$(A^2)$-$(A^3)$-$(A^4)$-$(A^5)$-$(A^6)$-$(A^7)$-$(A^8)$-$(A^9)$-$(A^{10})$-$(A^{11})$-$(A^{12})$-Gln-$(Xaa)_m$ (SEQ. ID. No. 11), and having amino acid substituents as described above wherein such peptides are radiolabeled by conjugation with or binding to a radioactive isotope. In a preferred embodiment, the peptide has the formula:

Phe-Gly-Gly-Phe-Thr-Gly-Ala-Arg-Lys-Ser-Ala-Arg-Lys-Tyr-Ala-Asn-Gln (SEQ ID No.: 6)

and the radiolabel is a radioisotope of iodine. In other preferred embodiments, the peptide is covalently linked to a radiolabel binding moiety and the radiolabel is a radioisotope of indium, gallium, technetium, rhenium or other useful radioisotope.

The invention also provides pharmaceutical compositions of the peptides of the invention. In a first aspect, the peptides of the invention are provided in a pharmaceutical composition comprising an acceptable carrier or diluent, or a pharmaceutical dosage form such as a vial of predetermined dose of the peptide, suspended in an injectable or inhalable vehicle such as sterile water or isotonic saline. Other dosage forms include tablets or capsules, particularly for synthetic mimetics more suitable for oral administration.

In a second aspect, such pharmaceutical compositions are provided in detectably-labeled embodiments, useful for diagnostic identification of sites of both normal and pathological peptide ligand receptor binding in vivo and in vitro. In such embodiments, the peptides of the invention are detectably labeled, for example, with a radioisotope such as I-123, I-125 or I-131, conjugated to the peptide via, inter alia, a tyrosine residue that is non-essential for receptor binding. Additional radioisotopes, such as In-111, Ga-67, Re-186, Re-188 and Tc-99m, can be conjugated to such peptides using methods well-understood in the art. In such embodiments, the pharmaceutical composition is radiolabeled to an appropriate specific activity, and administered to an animal, preferably a human, at a diagnostically-effective and non-toxic dose. Methods and routes of administration may be selected by those with skill in the art based on well-established techniques and in a clinically-appropriate fashion. Alternatively, the radiolabeled ligands can be used to identify specific brain regions where the ligand receptor is present.

DESCRIPTION OF THE DRAWINGS

FIGS. 1A and 1B illustrate the nucleotide (SEQ. ID No.: 3) and amino acid (SEQ ID No.: 4) sequences of the mammalian anti-opioid receptor of the invention.

FIGS. 2A and 2B present an amino acid sequence comparison between the novel mammalian OFQR protein of the invention (designated LC132) and the rat µ-opioid receptor, and the mouse δ- and κ-opioid receptor proteins.

FIG. 7 is a comparison of the amino acid sequence of orphanin FQ (OFQ) and opioid receptor binding peptides; identical amino acid residues shared between the peptides are shown in boldface.

FIG. 14 is a graph that demonstrates reversal of morphine analgesia in animals by comparing tail withdrawal latency time in animals that have received varying doses of OFQ.

DETAILED DESCRIPTION OF THE PREFERRED EMBODIMENTS

Figure 3:
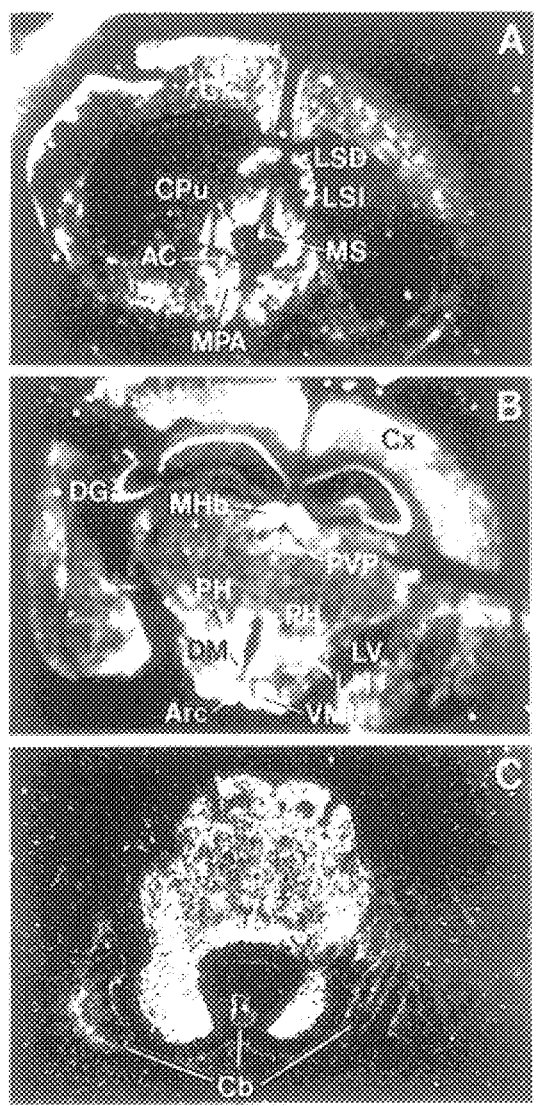
FIGS. 3A, B and C illustrate in situ hybridization of rat brain sections with a nucleic acid hybridization probe specific for the mammalian OFQR of the invention.

The present invention is a method of antagonizing a physiologic effect of an opioid in an animal. As used in this specification, the terms "opiate" and "opioid" will be used as defined in Goodman and Gilman, The Pharmacological Basis of Therapeutics, 7th edition (hereinafter "Goodman and Gilman"), page 492. "Opiate" will be used to designate drugs derived from opium, such as morphine, codeine, and the many semi-synthetic congeners of morphine. "Opioid" will refer in a generic sense to all drugs or biological substances, natural and synthetic, with morphine-like actions. Hence the term "opioid" will include such synthetic morphine-like compounds as propoxyphene, as well as the endogenous opioid peptides that include the enkephalins, endorphins, and dynorphins.

The term "anti-opioid" refers to a peptide or other chemical compound that antagonizes the physiological effects of an opioid. "Antagonizes" refers to a biochemical or pharmaceutical reversal or reduction of a physiologic effect. The peptides of the present invention specifically bind to an anti-opioid receptor, which is believed to exist separate from opioid receptors, and mediates physiologic antagonism of effects mediated by opioid receptors.

"High specificity" (selectivity) refers to binding with high affinity to a receptor, which in this specification shall be defined to bind with a $K_i$ or $IC_{50}$ of about 100 nM or less. In more particular embodiments wherein specific binding is particularly high, the $K_i$ or $IC_{50}$ is 10–100 nM, particularly 0.1 to 10 nM, and especially 0.1 nM or less. Methods of determining binding selectivity are well known, and for example are described in Goldstein, TIPS Reviews, pages 456–459, December 1987 (Vol. 8), which is incorporated by reference. The expression $K_i$ is used as known in the art, and defined in J. Neurochem. 64: 18–23 (1995), which is incorporated by reference. See particularly Table 1 of that incorporated reference.

As described in the incorporated reference, $K_i$ values are calculated based on the $IC_{50}$ value for the high affinity site using the equation of Cheng and Prusoff, Biochem. Pharmacol. 22: 3099–3108 (1973): $K_i = IC_{50}/(1+[L]/K_D)$, where $IC_{50}$ is the concentration of unlabeled ligand that inhibits 50% of the labeled ligand (L) binding, [L] is the total concentration of ligand provided in the assay, and the $K_D$ is defined as the dissociation constant. $IC_{50}$ may be determined by the method described in Example 12. The dissociation constant $K_D$ is defined at Goodman and Gilman, page 41, which is incorporated by reference. Determination of the dissociation constant for an agonist receptor complex is well known in the art, and is, for example, determined by the methods described in Munson, Principles of Pharmacology (Chapman & Hall), 1995, Chapter 1, which is incorporated by reference. Determination of the affinity constant is particularly discussed at pages 17–18 thereof, and is a technique well known in the art. It may be determined from a conventional Scatchard analysis, wherein the slope of the Scatchard line is $-1/K_D$. Alternatively, $K_D$ is determined from kinetic experiments in which $K_D = k_1/k_2$ where $k_1$ is the dissociation rate constant and $k_2$ is the association rate constant.

A physiologic effect of an opioid includes (without limitation) one or more of those biochemical changes and/or clinical signs and symptoms noted after administration of an opioid to an animal, and includes those effects enumerated at pages 497–504 of Goodman and Gilman. Such effects include one or more of inhibition of cellular cAMP accumulation, analgesia, drowsiness, changes in mood (including euphoria), pupillary responses, respiratory depression, nausea, peripheral vasodilation, hypothermia, and reduction of gastrointestinal motility. The invention also provides methods for designing OFQ receptor ligands and analogues, derivatives and mimetics thereof, using the amino acid sequence of the peptide ligands of the invention. Also encompassed within the scope of this invention are such analogues, derivatives and mimetics produced by the methods of the invention.

In a second aspect, the invention provides nucleic acids encoding a novel mammalian opioid-specific receptor protein having an amino acid sequence identified as SEQ ID No.: 4, recombinant eukaryotic expression constructs capable of expressing the novel mammalian opioid-specific receptor of the invention in cultures of transformed cells, as well as cultures of transformed eukaryotic cells that synthesize the receptor of the invention. The invention also provides homogeneous compositions of the receptor protein having an amino acid sequence identified as SEQ ID No.: 4, and antibodies against and epitopes of the receptor protein of the invention. Methods for characterizing these receptor proteins and methods for using these proteins in the development of agents having pharmacological uses related to these receptors are also provided by the invention.

In this aspect of the invention is provided a nucleic acid having a nucleotide sequence encoding a mammalian OFQ receptor. In a preferred embodiment, the nucleic acid encodes 1452 nucleotides of the cDNA comprising 1101 nucleotides of coding sequence, 181 nucleotides of 5' untranslated sequence and 170 nucleotides of 3' untranslated sequence, depicted in FIGS. 1A and 1B and identified as SEQ ID No.: 3. Encompassed in this aspect of the invention is the disclosed sequence and allelic variants of this sequence, either naturally occurring or the product of in vitro chemical or genetic modification.

The corresponding receptor protein, having the deduced amino acid sequence shown in FIGS. 1A and 1B and identified as SEQ ID No.: 4, is also an aspect of the invention. A particular embodiment of this aspect of the invention is a homogeneous composition of the 47 kD mammalian OFQ receptor protein and derivatives thereof, said size being understood to be the size of the protein before any post-translational modifications. The amino acid sequence of the 47 kD receptor protein is depicted in FIGS. 1A and 1B and identified as SEQ ID No.: 4.

This invention provides both nucleotide and amino acid sequence probes derived from the sequences herein provided, isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clones embodying this aspect of the invention, and oligonucleotide and other synthetic probes synthesized chemically using the nucleotide sequence information of cDNA or genomic clone embodiments of the invention.

The present invention also includes synthetic peptides made using the nucleotide sequence information comprising the cDNA embodiments of the receptor protein embodiments of the invention. The invention includes either naturally occurring or synthetic peptides which may be used as antigens for the production of receptor-specific antibodies, or useful as competitors of receptor molecules for agonist, antagonist or drug binding, or to be used for the production of inhibitors of the binding of agonists or antagonists or analogues thereof to such OFQ receptor molecules. Particularly preferred embodiments of this aspect of the invention are such peptides that interact with the peptide ligand embodiment of the invention and enhance or inhibit peptide ligand binding to the receptor protein.

The present invention also provides antibodies against and epitopes of the mammalian opioid receptor molecules of the invention, including antisera and both polyclonal and monoclonal embodiments of such antibodies and hybridoma cell lines producing such monoclonal antibodies.

The present invention provides recombinant expression constructs comprising a nucleic acid encoding a mammalian OFQ receptor of the invention wherein the construct is capable of expressing the encoded OFQ in cultures of cells transformed with the construct. Preferred embodiments of such constructs comprise the OFQ receptor cDNA depicted in FIGS. 1A and 1B (SEQ ID No.: 3), such constructs being capable of expressing the OFQ receptor encoded therein in cells transformed with the construct.

The invention also provides cultures of cells transformed with the recombinant expression constructs of the invention, each such culture being capable of and in fact expressing the mammalian OFQ receptor encoded in the transforming construct; and protein preparations of prokaryotic and eukaryotic cell membranes containing the OFQR protein of the invention, derived from cultures of prokaryotic or eukaryotic cells, respectively, transformed with the recombinant expression constructs of the invention.

The invention also provides methods for screening compounds for their ability to inhibit, facilitate or modulate the biochemical activity of the mammalian OFQ receptor molecules of the invention, for use in the in vitro screening of novel agonist and antagonist compounds. In preferred embodiments, cells transformed with a recombinant expression construct of the invention are contacted with such a compound, and the binding capacity of the compounds, as well as the effect of the compound on binding of other, known opioid agonists and antagonists, is assayed. Additional preferred embodiments comprise quantitative analyses of such effects. The invention specifically provides a method for screening a compound for a capacity to bind to a mammalian OFQ receptor in cells expressing the receptor, and using a competitive assay between the compound to be tested and the peptide ligands of the invention. The method comprises the steps of:

(a) transforming a culture of eukaryotic or prokaryotic cells with a recombinant expression construct capable of expressing a mammalian OFQ receptor having an amino acid sequence identified as SEQ ID No.: 4, wherein the cells of the transformed cell culture express the receptor;

(b) assaying the transformed cell culture for binding of an amount of a detectably-labeled peptide according to claim 1 in competition with varying amounts of the compound; and (c) determining whether the compound competitively binds to the receptor by calculating the extent of inhibition of binding of the detectably-labeled peptide in the presence of the compound.

In additional embodiments of this method is included the additional step of:

(d) comparing the binding capacity of the compound with the binding capacities of additional compounds that are known to bind to mammalian opioid receptors, wherein said additional compounds comprise naturally-occurring and synthetic opioid receptor agonists and antagonists.

The present invention is also useful for the detection of analogues, agonists or antagonists, known or unknown, of the mammalian OFQ receptor of the invention, either naturally occurring or embodied as a drug. In preferred embodiments, such analogues, agonists or antagonists may be detected in blood, saliva, semen, cerebrospinal fluid, plasma, lymph, or any other bodily fluid. In particularly preferred embodiments the peptide ligands of the invention are used in competitive binding assays to quantitatively evaluate novel ligand binding to the OFQ receptor.

Specific preferred embodiments of the present invention will become evident from the following more detailed description of certain preferred embodiments and the claims. The term "novel mammalian OFQ receptor" and "OFQR" as used herein refers to proteins comprising or consisting essentially of, and having substantially the same biological activity as, the protein encoded by the nucleic acid depicted in FIGS. 1A and 1B (SEQ ID No.:3). This definition is intended to encompass natural allelic variations in the disclosed OFQR sequence. Cloned nucleic acid provided by the present invention may encode OFQR protein of any species of origin, including, for example, mouse, rat, rabbit, cat, and human, but preferably the nucleic acid provided by the invention encodes OFQR receptors of mammalian, most preferably rat and human, origin.

The nucleic acids of the invention comprise nucleic acid hybridization probes comprising DNA or RNA consisting essentially of the nucleotide sequence of the OFQ receptor, depicted in FIGS. 1A and 1B (SEQ ID No.:3), or any portion thereof effective in nucleic acid hybridization. Mixtures of such nucleic acid hybridization probes are also within the scope of this embodiment of the invention. Nucleic acid probes as provided herein are useful for detecting OFQ receptor gene expression in cells and tissues using techniques well-known in the art, included but not limited to Northern blot hybridization, in situ hybridization and Southern hybridization to reverse transcriptase-polymerase chain reaction product DNAs. The probes provided by the present invention, including oligonucleotide probes derived therefrom, are also useful for Southern hybridization of mammalian, preferably human, genomic DNA for screening for restriction fragment length polymorphisms (RFLPs) associated with certain genetic disorders.

The invention provides an isolated and purified, naturally-occurring, endogenous mammalian peptide ligand that specifically binds to the OFQ receptor of the invention. For the purposes of this invention it will be understood that the peptide is any biologically active molecule that specifically binds to an OFQ receptor of the invention. The peptides of the invention include synthetic embodiments of the naturally-occurring peptide ligand isolated as described herein, as well as analogues, derivatives and variants of this peptide that specifically bind to the OFQR. Such analogues include substitution variants, wherein an amino acid is substituted conservatively with another amino acid that does not ablate the specific binding properties of the peptide ligand. Specifically provided are substitution variants wherein the substituted amino acid is Leu$^{14}$, wherein this residue is substituted with tyrosine.

Each peptide ligand of the invention is comprised of a sequence of amino acids. The term amino acid as used in this invention is intended to include all L- and D-amino acids, naturally occurring and otherwise.

Generally, those skilled in the art will recognize that peptides as described herein may be modified by a variety of chemical techniques to produce compounds having essentially the same activity as the unmodified peptide, and optionally having other desirable properties. For example, carboxylic acid groups of the peptide, whether carboxyl-terminal or sidechain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as a 5- or 6-membered ring. Amino groups of the peptide, whether amino-terminal or sidechain, may be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide.

Hydroxyl groups of the peptide sidechain may be converted to $C_1$–$C_{16}$ alkoxy or to a $C_1$–$C_{16}$ ester using well-recognized techniques. Phenyl and phenolic rings of the peptide sidechain may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the peptide sidechains can be extended to homologous $C_2$–$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced binding and/or stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

It will be apparent to one skilled in the art that the anti-opioid activity of the peptides disclosed herein lies not in the precise amino acid sequence, but rather in the epitopes inherent in the amino acid sequences encoded by the DNA sequences. It will therefore also be apparent that it is possible to recreate the anti-opioid activity of one of these peptides by recreating the epitope, without necessarily recreating the exact amino acid sequence. This could be achieved either by directly synthesizing the peptide (thereby circumventing the need to use the DNA sequences) or, alternatively, by designing a nucleic acid sequence that encodes for the epitope, but which differs, by reason of the redundancy of the genetic code, from the sequences disclosed herein. Similarly, the OFQR DNA sequence may also be varied, while still producing a functional OFQR protein.

Accordingly, the degeneracy of the genetic code further widens the scope of the present invention as it enables major variations in the nucleotide sequence of a DNA molecule while maintaining the amino acid sequence of the encoded protein. The genetic code and variations in nucleotide codons for particular amino acids is presented in Tables 1 and 2. Based upon the degeneracy of the genetic code, variant DNA molecules may be derived from the DNA sequences disclosed herein using standard DNA mutagenesis techniques, or by synthesis of DNA sequences.

TABLE 1

The Genetic Code

| First Position (5' end) | Second Position | | | | Third Position (3' end) |
|---|---|---|---|---|---|
| | T | C | A | G | |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ocre termination triplet, and "Stop (amb)" for the amber. ATG is the most common initiator codon; GTG usually codes for valine, but it can also code for methionine to initiate an mRNA chain.

TABLE 2

The Degeneracy of the Genetic Code

| Number of Synonymous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

Additionally, standard mutagenesis techniques may be used to produce peptides which vary in amino acid sequence from the peptides encoded by the DNA molecules disclosed herein. However, such peptides will retain the essential characteristic of the peptides encoded by the DNA molecules disclosed herein, i.e. the ability to antagonize opioid action by binding to the OFQR. This characteristic can readily be determined by the assay technique described herein for cAMP accumulation. Screening for retention of anti-opioid effects is similarly achieved in a forthright manner using the methods of Examples 8–11 below. Variant peptides include those with variations in amino acid sequence, including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

In order to maintain a functional peptide, preferred peptide variants will differ by only a small number of amino acids from the peptides encoded by the native DNA sequences. Preferably, such variants will be amino acid substitutions of single residues. Substitutional variants are those in which at least one residue in the amino acid sequence has been removed and a different residue inserted in its place. Such substitutions generally are made in accordance with the following Table 3 when it is desired to finely modulate the characteristics of the protein. Table 3 shows amino acids which may be substituted for an original amino acid in a protein and which are regarded as conservative substitutions. As noted, all such peptide variants are tested to confirm that they retain the ability to antagonize opiate action.

TABLE 3

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in biological activity may be made by selecting substitutions that are less conservative than those in Table 2, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Peptidomimetic and organomimetic embodiments are also hereby explicitly declared to be within the scope of the present invention, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides of this invention having substantial biological activity. For computer modelling applications, a pharmacophore is an idealized, three-dimensional definition of the structural requirements for biological activity. Peptido- and organomimetics can be designed to fit each pharmacophore with current computer modelling software (computer aided drug design). The degree of overlap between the specific activities of pharmacophores remains to be determined. It will be understood that mimetics prepared using such techniques that specifically bind to the OFQ receptor and developed using the peptide ligands of the invention will fall within the scope of the appended claims.

The peptides provided by the present invention can be chemically synthesized by any of a number of manual or automated methods of synthesis known in the art. Automated synthetic routines such as those available for use with automated peptide synthesizers are also intended to come within the scope of the present invention. Chemical derivatization, using the methods disclosed in this specification or other methods well known in the art, of naturally-occurring peptides or peptides purified from mixtures of protein degradation products, degraded by enzymatic or chemical means, are also within the scope of this invention, as are peptides made by molecular or genetic engineering means. Preferably, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxymethylpolystyrene (HMP) or Sasrin™ resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. (1989, *Solid Phase Peptide Synthesis,* IRL Press: Oxford).

Sasrin™ resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5–3 hours at room temperature.

Crude peptides are purified by preparative high pressure liquid chromatography (HPLC) using a Waters Delta-Pak C18 column and gradient elution with 0.1% TFA in water modified with acetonitrile. After column elution, acetonitrile is evaporated from the eluted fractions, which are then lyophilized. The identity of each product so produced and purified is confirmed by fast atom bombardment mass spectroscopy (FABMS) or electrospray mass spectroscopy (ESMS).

The production of proteins such as the OFQ receptor proteins of the invention from cloned genes by genetic engineering means is well known in this art. The discussion which follows is accordingly intended as an overview of this field, and is not intended to reflect the full state of the art.

DNA encoding an opioid receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from the receptor (OFQR) disclosed herein. Probes may be labeled with any detectable group and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an OFQR as provided herein. See U.S. Pat. Nos. 4,683,195 to Mullis et al. and 4,683,202 to Mullis.

OFQR protein may be synthesized in host cells transformed with a recombinant expression construct comprising a nucleic acid encoding the OFQ receptor cDNA. For the purposes of this invention, a recombinant expression construct is a replicable DNA construct in which a nucleic acid encoding an opioid receptor is operably linked to suitable control sequences capable of effecting the expression of the opioid receptor in a suitable host. Generally, control sequences include a transcriptional promoter, an optional operator sequence to control transcription, a sequence encoding suitable mRNA ribosomal binding sites, and sequences which control the termination of transcription and translation. See, Sambrook et al., 1990, *Molecular Cloning: A Laboratory Manual* (Cold Spring Harbor Press:

New York).

Vectors useful for practicing the present invention include plasmids, viruses (including phage), retroviruses, and integratable DNA fragments (i.e., fragments integratable into the host genome by homologous recombination). A preferred vector is RcRVS (Invitrogen, San Diego, Calif.).

Cultures of cells derived from multicellular organisms are a desirable host for recombinant opioid receptor protein synthesis. Transformed host cells are cells which have been transformed or transfected with recombinant expression constructs made using recombinant DNA techniques and comprising nucleic acid encoding an amino acid transporter protein. Transformed host cells may express the OFQR protein; when expressed, the OFQ receptor of the invention will typically be located in the host cell membrane. See, Sambrook et al., ibid. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, mouse Ltk cell lines and WI138, BHK, COS-7, CF, and MDCK cell lines. CHO cells, COS-7 cells and Ltk cells are preferred.

The recombinant expression constructs of the present invention are useful to transform cells which do not ordinarily express an OFQ receptor to thereafter express the receptor. Such cells are useful as intermediates for making cell membrane preparations useful for receptor binding activity assays, which are in turn useful for screening drugs or new peptides made in accordance with the present invention. The recombinant expression constructs of the present invention thus provide a method for obtaining reagents for screening potentially useful peptides and other drugs at advantageously lower cost than conventional animal screening protocols. While not completely eliminating the need for ultimate in vivo activity and toxicology assays, the constructs and cultures of the invention provide an important first screening step for the vast number of potentially useful psychoactive drugs synthesized, discovered or extracted from natural sources each year.

The recombinant expression constructs of the present invention are useful to detect, isolate, characterize and identify other novel endogenous receptors for anti-opioid agonists (such as OFQ) and antagonists found in plasma, serum, lymph, cerebrospinal fluid, seminal fluid, or other potential sources of such compounds.

The utility of the present invention for using the nucleic acids of the invention to produce cell membranes containing the receptor protein encoded thereby, and the demonstrated utility of this aspect of the invention to permit the isolation, characterization and identification of a novel peptide, termed orphanin FQ (OFQ) herein, as an endogenous receptor-binding ligand, enables rational drug design of novel therapeutically-active drugs using currently-available techniques (see Walters, "Computer-Assisted Modeling of Drugs", in Klegerman & Groves, eds., 1993, *Pharmaceutical Biotechnology,* Interpharm Press: Buffalo Grove, Ill., pp. 165–174).

The invention provides homogeneous compositions of a novel mammalian receptor protein produced by transformed eukaryotic cells as provided herein. Each such homogeneous composition is intended to be comprised of the OFQR protein that comprises at least 90% of the protein in such homogenous composition. The invention also provides membrane preparations from cells expressing the OFQR protein as the result of transformation with a recombinant expression construct, as described herein.

Mammalian receptor proteins made from cloned genes in accordance with the present invention may be used for screening analogues of an anti-opioid system that operates in parallel with and in functional antagonism to the opioid system. The receptor proteins may also be useful to find agonists or antagonists of opioid binding, or for determining the amount of such agonists or antagonists that are present in a solution of interest (e.g., blood plasma, cerebrospinal fluid or serum). For example, host cells may be transformed with a recombinant expression construct of the present invention, a mammalian OFQR expressed in those host cells, and the cells or membranes thereof used to screen compounds for their effect on anti-opioid receptor binding activity. By selection of host cells that do not ordinarily express an OFQR, pure preparations of membranes containing the transporter can be obtained.

The invention also provides ligands for such OFQR proteins, including naturally-occurring ligands and synthetic embodiments thereof. Methods for identifying other, alternative ligands, and agonists and antagonists of OFQ peptide ligand binding are also provided by the invention. Such methods include competitive binding assays, wherein the peptide ligands of the invention are detectably labeled and incubated under competitive binding conditions with varying amounts of any putative ligand compound to be tested. The extent of inhibition of labeled ligand binding is useful in characterizing the extent and affinity of binding of novel ligands to the OFQR. Specificity of binding can also be determined using such assays. Preferably, the peptide ligand of the invention being used in such competition experiments is detectably labeled with a radioisotope, such as I-123, I-125 and I-131.

The invention also provides antibodies that are immunologically reactive to the opioid receptor protein or epitopes thereof provided by the invention. The antibodies provided by the invention may be raised using methods well known in the art.

The present invention also provides monoclonal antibodies that are immunologically reactive with an epitope derived from an OFQ receptor of the invention, or fragment thereof. Such antibodies are made using methods and techniques well known to those of skill in the art. Monoclonal antibodies provided by the present invention are produced by hybridoma cell lines, that are also provided by the invention and that are made by methods well known in the art.

The ligands of the invention are useful as diagnostic and therapeutic agents when constituted as pharmaceutical compositions with the appropriate carriers or diluents. In diagnostic embodiments, detectably-labeled peptide ligands are used in methods for diagnosing diseases or pathological conditions related to ligand binding of OFQ receptors in vivo. Similarly, therapeutic methods of treatment are encompassed by the invention and provided using pharmaceutical compositions of such peptides administered in vivo in therapeutically-effective amounts.

Preparation of pharmaceutically acceptable compositions of the peptides of the present invention can be accomplished using methods well known to those with skill in the art. Any of the common carriers such as sterile saline solution, plasmas, etc., can be utilized with the peptides provided by the invention. Routes of administration include but are not limited to oral, intracranial ventricular (icv), intrathecal (it), intravenous (iv), parenteral, rectal, topical ophthalmic, subconjunctival, nasal, aural and transdermal. Peptides of the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

Embodiments of the invention comprising medicaments can be prepared with conventional pharmaceutically acceptable carriers, adjuvants and counterions as would be known to those of skill in the art. The medicaments are preferably in the form of a unit dose in solid, semi-solid and liquid dosage forms such as tablets, pills, powders, liquid solutions or suspensions, and injectable and infusible solutions, for example a unit dose vial. Effective dosage ranges included in the unit dose container vary from about 100 µg/kg to about 10 mg/kg of body weight are contemplated.

The invention also provides methods for detecting the amount of an analyte in a solution wherein the analyte is an endogenous peptide ligand of the invention in a biological sample, such as blood, serum, plasma or cerebrospinal fluid. In such methods is provided a first mixture comprised of cells or membranes heterologously expressing the OFQ opioid receptor of the invention, a second mixture comprised of a standard amount of a detectably-labeled embodiment of the peptide ligands of the invention, and a third mixture comprised of a diagnostically-significant tissue sample or bodily fluid. From these mixtures is produced a specific binding reaction mixture by contacting the first, second and third mixtures and incubating the reaction mixture for a time sufficient to allow binding between the peptide ligand and the OFQ receptor. The extent of the binding reaction is determined by calculating the amount of the detectably-labeled peptide ligand of the invention bound to the OFQ receptor, and comparing the amount of binding of the peptide ligand to the OFQ receptor in the presence of the tissue sample or bodily fluid of the third provided mixture with the amount of binding found in the absence of the tissue sample or bodily fluid of the third provided mixture.

Throughout these examples, injections are sometimes given intrathecally or intraventricularly. The intrathecal injection method allows the application of small quantities of drug directly into the spinal cord, without surgical intervention. The mouse is briefly exposed to halothane, immediately prior to all injections.

Intrathecal injection is achieved with disposable 30 g, ½ inch needles mated to a 10 µl luer tip syringe (Hamilton, Reno, Nev.) are used. Drug is administered in artificial cerebral spinal fluid and injection volumes are 2–5 µl. The mouse is placed on a flat surface, with its head in a towel cupped gently with the heel of the palm, and the thumb and forefinger lightly pushing down on the iliac crests with enough force to stretch the skin across the lower back. The needle is inserted into the tissue just medial to the L5 spinous process so that it enters the groove between the spinous and transverse processes. This site maximizes vertebral accessibility and minimizes the possibility of spinal damage (into the cauda equina). The needle is then moved carefully forward to the intervertebral space as the angle of the syringe is decreased from about 30° to 15°. The tip of the needle is inserted so that approximately 0.5 cm is within the vertebral column which is reliably indicated by a flick of the mouse's tail.

In a human, conventional lumbar puncture with a spinal needle can be used to access the epidural or intrathecal space.

For icv injections, a 26 g ½ inch needle is fitted with a piece of polyethylene tubing so that 3 mm of uncovered needle enter the mouse's skull. (The sleeve ensures that the depth of the needle is appropriate for the depth of the lateral ventrical). Mice are briefly anesthetized with halothane. The needle is held at a 45° angle and inserted at Bregma, 1–2 mm lateral to midline. The needle readily punctures the skull at this suture, so no incision is required for accurate placement. The needle tip is towards the tail, and the 3 mm depth allows direct placement of the drug into a lateral ventricle.

The Examples which follow illustrate specific embodiments of the invention, and various uses thereof. They are set forth for explanatory purposes only, and are not to be taken as limiting the invention.

EXAMPLE 1

Isolation of a Mammalian Opioid Receptor Probe by Random PCR Amplification of Rat Brain-derived cDNA Using Degenerate Oligonucleotide Primers In order to clone novel mammalian G-protein coupled receptors, cDNA prepared from RNA from different regions of mammalian (rat) brain was used as template for a polymerase chain reaction (PCR)-based random cloning experiment. PCR was performed using a pair of degenerate oligonucleotide primers derived from a mouse δ-opioid receptor (Kieffer et al., 1992, Proc. Natl. Acad. Sci. USA 89: 12048–12052; Evans et al., 1992, Science 258: 1952–1955). PCR products obtained in this experiment were characterized by nucleotide sequencing and used to isolate a full-length cDNA from a rat brain cDNA library.

The PCR amplification experiments were performed as described in co-owned and co-pending U.S. Ser. No. 08/149,093, incorporated by reference, using the following primers:

Primer III (sense):

ATGAATTCAC(G/A/C/T)(A/G)T(G/C)ATGAG(C/T)GT(G/C)GAC(C/A)G(C/A)TA    (SEQ ID NO:1)

and

Primer VII (antisense):

TTGTCGAC(G/A)TA(G/A)AG(A/G)A(T/C)(G/A/C/T)GG(G/A)TT    (SEQ ID NO:2).

Amplified products of the PCR reaction were separated on a 1.0% agarose gel (see Sambrook et al., ibid.), and fragments ranging in size from 400 basepairs (bps) to 750 bp were subcloned in the plasmid vector pBluescript (Stratagene, LaJolla, Calif.). A multiplicity of bacterial colonies comprising each of the subcloned fragments were used to make bacterial colony lifts on nitrocellulose filters using conventional techniques (see Sambrook, et al., ibid.). Such filters were hybridized with a [$^{32}$P]-dCTP-labeled radioactive nucleic acid probe comprising a full-length mouse δ-opioid receptor cDNA at a concentration of $1\times10^6$ cpm/mL under low stringency hybridization conditions [35% formamide, 5× standard citrate saline (SSC; wherein 1× SSC is 0.15M NaCl/0.015M sodium citrate, pH 7.0), 5× Denhardt's solution (wherein 1× Denhardt's solution is 0.02 g/mL each of bovine serum albumin, Ficoll and polyvinylpyrrolidone)] at 37° C. overnight. After hybridization, the filters were washed in a solution of 2× SSC/0.1% sodium dodecyl sulfate (SDS) at 55° C. and then exposed to X-ray film (XAR-5, Eastman-Kodak, Rochester, N.Y.) for 2 days at −70° C. using tungsten-impregnated intensifying screens (DuPont-NEN, Wilmington, Del.). Plasmid DNA from hybridizing clones was purified and the nucleotide sequence of the insert cDNA determined by the dideoxynucleotide chain termination method (Sanger et al., 1977, Proc. Natl. Acad. Sci. USA 74: 5463–5467) using Sequenase® (U.S. Biochemical Corp., Cleveland, Ohio).

EXAMPLE 2

Isolation of a Novel Mammalian Opioid Receptor cDNA

One of the PCR products (termed LC132) was isolated and sequenced in this way and found to have a high degree of homology to the mouse δ-opioid receptor sequence (Evans et al., ibid. and Kieffer et al., ibid.). A full-length cDNA clone corresponding to this PCR fragment was isolated from a cDNA library prepared in the cloning vector λgt11 comprising oligo(dT)-primed rat brain cDNA, as described in co-owned and co-pending U.S. Ser. No. 07/149,093.

Nucleotide sequence analysis performed essentially as described (see, Sambrook, ibid.) revealed the sequence shown in FIGS. 1A and 1B (SEQ ID No.:3). The putative protein product of the gene is also shown in FIGS. 1A and 1B (SEQ ID No.:4). The sequence was found to have an open reading frame comprising 1101 nucleotides encoding a protein 367 amino acids in length, and having a predicted molecular weight of 47 kilodaltons prior to post-translational modification. The sequence immediately 5' to the proposed initiation codon was found to contain several translation termination codons in-frame with the open reading frame, supporting the assignment of the translation start site. Predicted transmembrane domains [using the algorithm of Eisenberg et al. (1984, J. Molec. Biol. 179: 125–142)] are boxed and identified by Roman numerals (I–VII), and three sites of possible N-linked glycosylation are identified in the amino-terminal portion of the protein with solid triangles. Potential protein phosphorylation sites found in predicted cytoplasmic loops are marked with an asterisk. Further, a pair of cysteine residues conserved among known opioid receptors were found in the first and second predicted extracellular loops. On the basis of this analysis, this cloned nucleic acid was determined to be a novel mammalian receptor related to opioid receptors, such as the μ, δ and κ receptors.

The predicted amino acid sequences of this novel receptor, the rat μ-opioid receptor (Chen et al., ibid.)., the mouse δ-opioid receptor (Evans et al, ibid. and Kieffer et al., ibid.) and the mouse κ-opioid receptor (Yasuda et al., ibid.) are aligned in FIG. 2. Overbars indicate predicted transmembrane regions I through VII in the protein product of the genes. Amino acid residues that are found in common between all four mammalian opioid receptors are presented in boldface.

Overall, the novel mammalian receptor disclosed herein had 47% overall identity with the other mammalian opioid receptors, which similarity rose to 67% when only the predicted transmembrane domains were considered. Comparisons were made individually at each transmembrane domain (TMI-TMVII), as an average over all transmembrane domains (TMavg) and as the average degree of amino acid sequence homology for each protein as a whole (avg/all). In total, 145 of the 367 residues are shared with the other mammalian opioid receptors, confirming the conclusion that the novel mammalian receptor disclosed herein is related to the opioid receptors. The inventors have now surprisingly discovered, however, that the receptor mediates an anti-opioid effect.

EXAMPLE 3

Construction of a Recombinant Expression Construct, DNA Transfection and Functional Expression of the Novel Mammalian Opioid Receptor In order to biochemically characterize the novel mammalian opioid receptor described in Example 2, and to confirm that it encodes a novel opioid receptor, the cDNA was cloned into a mammalian expression construct, the resulting recombinant expression construct transfected into COS-7 cells (for transient expression assays) and mouse Ltk⁻ cells (for stable expression assays), and cell membranes (COS-7) or cell lines (Ltk⁻) were generated that expressed the receptor protein in cellular membranes at the cell surface. Such cells and membranes isolated from such cells were used for biochemical characterization experiments as described in U.S. Ser. No. 149,093.

The entire coding region of the receptor cDNA insert was subcloned into the RcRSV vector (Invitrogen, San Diego, Calif.) using conventional techniques (see Sambrook et al., ibid.). Such recombinant expression constructs were introduced into COS-7 cells using the calcium-phosphate precipitation technique (Chen & Okayam, 1987, Molec. Cell Biol. 7: 2745–2752), the transfected cells allowed to express the receptor for between 24–96 hours, and then cell membranes containing the receptor were isolated. The protein concentration was adjusted to a 15–80 μg/sample for each of the binding studies described below.

These recombinant expression constructs were also introduced into Ltk⁻ cells using the calcium-phosphate precipitation technique, and stably-transfected clones were selected by growth in the mammalian neomycin analog G418 (Grand Island Biological Co., Long Island, N.Y.), as the vector RcRSV contains a functional copy of a bacterial neomycin resistance gene. Stable cells lines were then selected for membrane binding studies based on mRNA expression levels of individual neomycin-resistant transfected clones determined by Northern analysis (see Sambrook et al., ibid.). Cell membranes were prepared and used as described above for COS-7 cell transfectants.

Specific binding assays using a variety of opioid receptor agonists and antagonists were performed on membranes from both transient and stable transfectants. Ligand binding experiments were performed essentially as described in Bunzow et al. (1988, Nature 336: 783–787), and U.S. Ser. No. 08/149,093). In binding experiments, increasing amounts of membrane protein (from 15–80 $\mu$g) were incubated with the radioactively-labeled opioid agonist or antagonist to be tested for 120 min at 22° C. in a total volume of 1 ml. However, in these experiments no specific binding was found for the following compounds (their known receptor binding specificities are noted in parentheses): [$^3$H]-Tyr-DAla-Gly-Met-Phe-Gly-ol (DAMGO; $\mu$-opioid receptor agonist), [$^3$H] -c[D-penicillamine$^2$, D-penicillamine$^5$]enkephalin (DPDPE; $\delta$ agonist), [$^3$H]-U-69,593 ($\kappa$ agonist), [$^3$H]-diprenorphine ($\mu$ agonist), [$^3$H]-bremacozine ($\kappa$ agonist), [$^3$H]-dihydromorphine ($\mu$ agonist), [$^3$H] -ethylketocyclazocine ($\kappa$ agonist) or [$^{125}$I]-$\beta$-endorphin. Although low levels of specific binding were seen using [$^3$H]-naloxone ($\mu$ antagonist), the significance of these results was compromised by the fact that untransfected COS-7 and Ltk⁻ cells also shown endogenous low levels of specific [$^3$H]-naloxone binding.

Figure 4A:
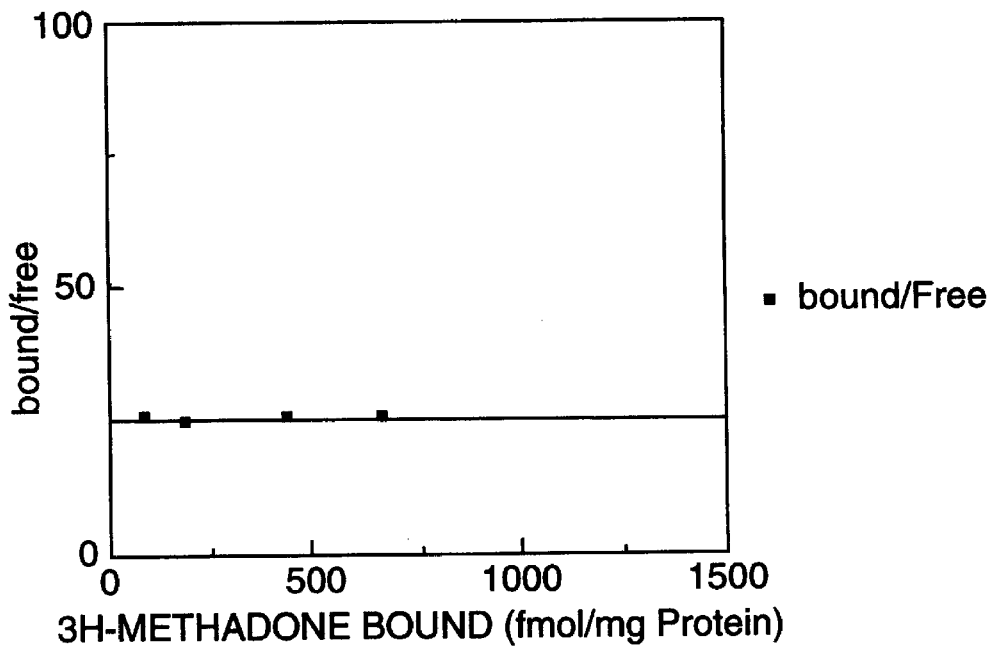
FIG. 4A presents affinity binding experiment results of $^3$H-methadone binding to COS-7 cells.
Figure 4B:
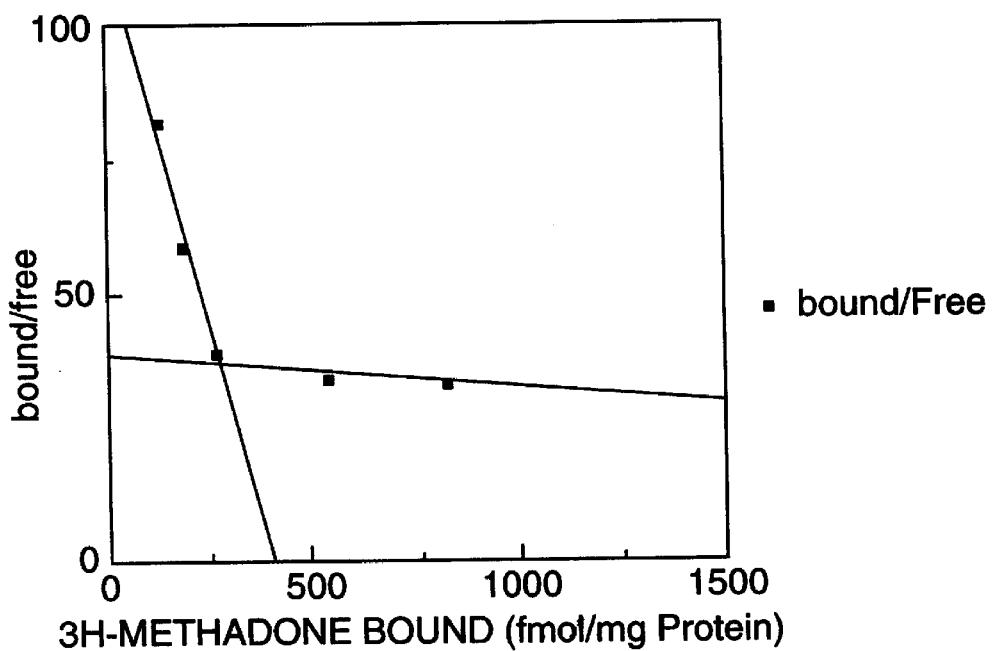
FIG. 4B presents affinity binding experiment results of $^3$H-methadone binding to COS-7 cells expressing the novel mammalian MSOR opioid receptor of the invention.

Surprisingly, however, specific binding was found using [$^3$H] -methadone. The results of Scatchard analysis of the methadone binding data are shown in FIGS. 4A and 4B.

For Scatchard analysis experiments, 0.25 ml aliquots of crude plasma membrane homogenate from transfected cell cultures was incubated in duplicate with increasing concentrations of [$^3$H]methadone (70.3 Ci/mmol; 10–3000 pM final concentration) under conditions described above. The estimated value for $B_{max}$ was derived from these data using the LIGAND computer program. FIG. 4A shows the results of radiolabeled methadone binding with untransfected COS-7 cells; similar results were found with Ltk⁻ cell membranes. These results demonstrate no or negligible amounts of endogenous methadone binding by these cell membranes. FIG. 4B shows the results using COS-7 cells transfected with the RcRSV-LC132 expression construct. The levels of specific binding shown in this graph correspond to a dissociation constant ($K_D$) of about $10^{-10}$M for methadone and a $B_{max}$ of about 400–450 fentomoles/$\mu$g protein for the novel mammalian opioid receptor expressed by these cells.

Thus, the novel mammalian opioid receptor disclosed herein has the heretofore unknown property of exhibiting specific binding to the opiate analog, methadone, while showing no specific binding to a variety of other known opioid receptor agonists and antagonists. These results support the conclusion that the receptor disclosed herein is a completely novel and heretofore unsuspected member of the opioid receptor family, termed herein therefore OFQ.

EXAMPLE 4

Brain Tissue Distribution of OFQR Expression

The distribution of mRNA corresponding to expression of the OFQ receptor gene in various regions of the rat brain was determined by in situ hybridization of rat brain slices, as described in U.S. Ser. No. 08/149,093.

Results of these experiments are shown in FIG. 3. Panel A shows a section through the frontal cortex, preoptic area and caudate putamen; Panel B shows a section through the hypothalamus, thalamus and hippocampus; and Panel C shows a section through the pons and cerebellum. These experiments localized high level OFQR expression in the hypothalamus (arcuate (Arc), posterior (PH), lateral (LH) and ventromedial (VMH) hypothalamic nuclei, Panel B), certain nuclei of the thalamus (paraventricular thalamic nuclei (PVP), Panel B), the medial habenula (MHb, Panel B), the CA regions of the hypothalamus, the dentate gyrus (DG, Panel B), the locus coeruleus and certain cortical areas (medial preoptic are (MPA), Panel A and the cortex (CX), Panel B), Virtually no signal was seen in the caudate putamen (Cpu, Panel A) or cerebellum (Cb, Panel C). Strong hybridization was also detected in sections of the brainstem (Panel C) and the spinal cord (not shown).

These results demonstrate that the OFQ receptor disclosed herein is expressed in rat brain in a variety of anatomically-distinct sites, suggesting an important role for this receptor in both higher brain function and central nervous system control of motor and sensory nerve signalling. The anti-opioid effects mediated by this receptor, however, were completely unpredictable.

EXAMPLE 5

Identification of an Endogenously-occurring Peptide Ligand for the OFQ Receptor Due to the high level of sequence homology between the OFQ receptor the and $\mu$-, $\delta$- and $\kappa$-opioid receptors found as disclosed in Example 2, it was appreciated that the novel receptor disclosed herein might specifically recognize an endogenous peptide ligand, and respond to binding such a ligand using a second messenger signalling system similar to those found associated with the previously-described opioid receptors. Since the OFQR had been found to be expressed in cells in the central nervous system in Example 4, and since OFQR mRNA is highly expressed in hypothalamus, porcine hypothalamic homogenates were screened for receptor binding activity. Inhibition of forskolin-stimulated, cyclic adenosine monophosphate (cAMP) accumulation in cells heterologously expressing OFQR was used as an assay, which assay had been used to characterize the interaction of opioid receptors and their ligands.

Acetic acid extracts of porcine hypothalamic tissues were prepared as follows. 4.5 kg of freshly frozen porcine hypothalamic tissue were extracted in 9 L of a solution of 0.5M acetic acid/10 mM ascorbic acid/1 mM EDTA. The extract was centrifuged to remove insoluble debris and the supernatant absorbed batchwise onto a $C_{18}$silica matrix. Unbound material was removed by washing with water, and specifically-bound material was then eluted in a solution of 80% methanol. A total of 2 L of methanolic eluate were then concentrated by rotary evaporation of a final volume of 44 mL, and material having a molecular weight less than 10 kilodaltons was obtained by ultrafiltration using an Amicon Centripep 10 column (Amicon, Beverl, Mass.). This material was applied in ten separate experiments to a cation exchange HPLC column (Protein Pak SP 8HR, 10×100 mm, Waters) equilibrated with 10 mM $NH_4COO$. The column was developer with a linear gradient of $NH_4COO$in 10% methanol at a flow rate of 1 mL/min; a total of 80 1 mL fractions were collected. 10% (100 $\mu$L) of each of 5 consecutive fractions were pooled and lyophilized, resulting in 16 pools. 5% of each pool was tested in duplicate for the capacity to inhibit forskolin-stimulated cAMP accumulation in cells heterologously expressing the OFQ opioid receptor.

Assays of ligand binding-associated inhibition of forskolin-stimulated cAMP accumulation in cells heterologously expressing the OFQ receptor were performed as follows. CHO cells, deficient in dihydrofolate reductase (dhfr⁻) were transfected with OFQR-encoding cDNA cloned into the expression vector pRcRSV (Invitrogen), as described in Example 3 above, using calcium phosphate co-precipitation (Okayama and Chen, ibid.) Stably-transfected clones were selected using G418, and screened for OFQ expression using a reverse transcriptase-PCR protocol (RT-PCR). One clone that tested positively for OFQR expression (LC-7) was used in ligand binding experiments.

For determination of cAMP levels, receptor-transfected CHO cells (i.e., LC-7) or untransfected CHO/dhfr⁻ cells, were plated in 24-well culture plates and grown to confluency. After removal of culture media, aliquots of HPLC fractions prepared as described above in a total volume of 0.2 mL DMEM containing 10 mM HEPES buffer, pH 7.4, 1 mM forskolin and 1 mM Ro 20–1724 (Rolipram, RBI) were added per well and cells incubated at 37° C. for 10 min. Cellular reactions were halted by the addition of 0.5 mL ice-cold ethanol, and plates were stored for 12 h or overnight at 80° C. Frozen plates were centrifuged and aliquots of the supernatant were removed and dried onto 96-well plates for cAMP determinations. cAMP determinations were performed using a commercially-available kit (Biotrak SPA, Amersham) essentially according to the manufacturer's instructions.

Figure 5:
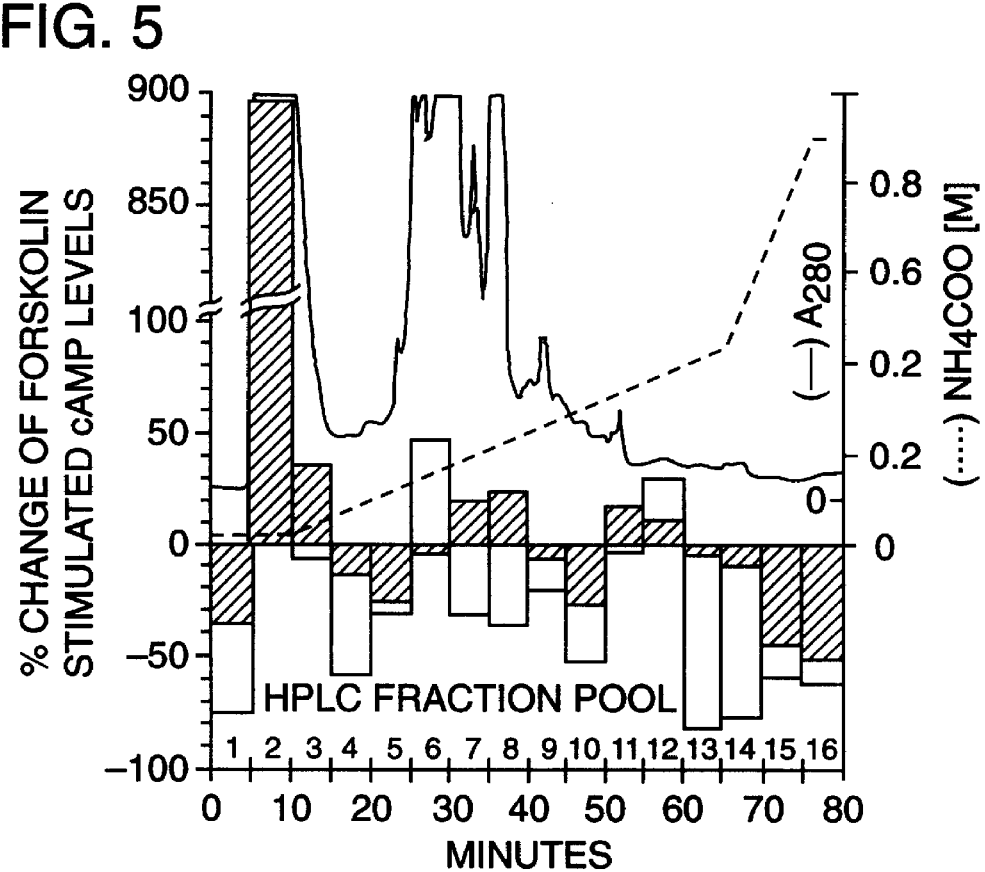
FIG. 5 shows the extent of inhibition of forskolin-stimulated cAMP accumulation in a CHO cell heterologously expressing OFQR of the invention by fractions of acetic acid-extracted peptides from porcine hypothalamus, wherein $A_{280}$ represents absorbance at 280 nm, shaded bars represent results obtained with untransfected CHO cells and open bars represent results obtained with OFQR transfected CHO cells.

The results of these experiments are shown in FIG. 5. Open bars represent results obtained with OFQ-expressing transfected CHO cells, and shaded bars represent results obtained with untransfected CHO cells. Pools 13 and 14 (corresponding to fractions 61–70) consistently showed adenyl cyclase inhibitory activity in transfected versus untransfected cells. The large increase in cAMP detected in fraction 2 is due to endogenous cAMP extracted from the tissue. Fractions 60–67 were found to contain most of the detected bioactivity, and were pooled for further purification by reverse-phase HPLC.

Figure 6:
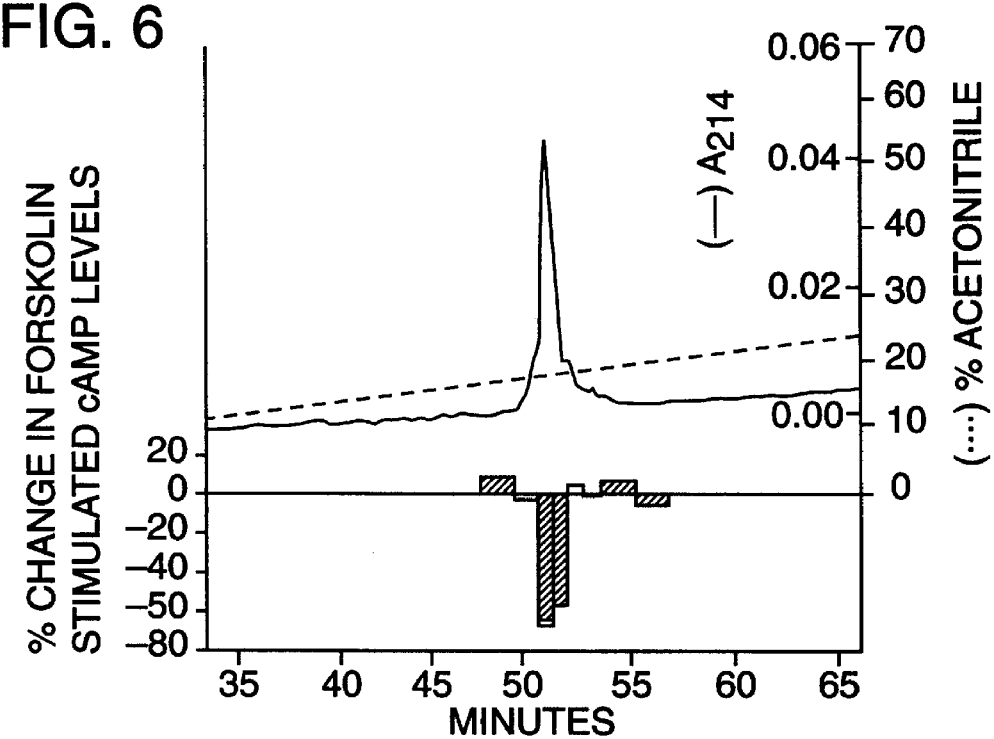
FIG. 6 shows the extent of inhibition of forskolin-stimulated cAMP accumulation in CHO cell heterologously expressing the OFQR of the invention by fractions of reverse-phase HPLC fractionated acetic acid-extracted peptides from porcine hypothalamus, wherein $A_{214}$ represents absorbance at 214 nm, and shaded bars represents results obtained with OFQR transfected CHO cells.

Reverse-phase HPLC was performed on pooled fractions 60–67 as follows. The complete bioactive material was loaded onto an octyl silica column (Superspher RP Select B, 2×125 mm, Merck) and eluted at a flow rate of 0.12 mL/min with a linear gradient of acetonitrile in 0.1% trifluoroacetic acid (TFA). Aliquots of fractions from this gradient were tested as described above, and the results of these assays shown in FIG. 6. Inhibition of forskolin-stimulated cAMP in OFQR-transfected CHO cells (shaded bars) was detected only in the major peak of eluted protein (measured as absorbance at 214 nm ($A_{214}$)).

The isolated material having adenyl cyclase inhibitory activity was analyzed by mass spectrometry and sequenced by Edman degradation. The material was determined to be a peptide having the sequence: Phe-Gly-Gly-Phe-Thr-Gly-Ala-Arg-Lys-Ser-Ala-Arg-Lys-Leu-Ala-Asn-Gln (SEQ ID No.: 5). (Abbreviations for amino acids can be found in Zubay, *Biochemistry* 2d ed., 1988, MacMillan Publishing: New York, p. 33). Final yields of this peptide were about 200 picomoles from 4.5 kg hypothalamic tissue (wet weight). A computer database search revealed that this peptide had not been reported, either as a unique entity or as part of a larger protein. This peptide is designated orphanin FQ (OFQ) herein.

The primary structure of this novel peptide was compared with the primary structure of a number of naturally-occurring opioid peptides, as shown in FIG. 7. The amino terminal tetrapeptide sequence motif YGGF of the known opioid receptor ligands is strikingly similar to the amino terminal sequence FGGF (SEQ. ID. No. 11) found in OFQ. Further, two clusters of basic amino acids found in the orphanin FQ peptide resemble the arrangement of positively-charged residues in Dynorphin A and β-Endorphin. However, none of these peptides could be shown to bind to OFQR, suggesting a structural/functional divergence of the orphanin FQ peptide from these other opioid receptor ligands.

In order to verify that the isolated material had the observed properties of the pooled fraction from which it is isolated, a synthetic peptide having the deduced sequence was made and was found to be identical to the isolated peptide in its elution profile in reverse-phase HPLC assay and in molecular weight as determined by mass spectrometry. Moreover, the synthetic peptide was also found to inhibit adenyl cyclase production in forskolin-stimulated CHO cells transfected with and heterologously expressing OFQR, having an $EC_{50}$ of 1.58 nM (±0.666 nM) and showing maximal inhibition (80%) at a concentration of about 100 nM. This high potency is comparable to that of other neuropeptides identified as the naturally-occurring ligands of other CNS-specific receptors. Thus, the isolated sequence, termed orphanin FQ herein, represents a novel endogenous peptide ligand for the OFQR.

To further characterize ligand binding of this novel ligand to OFQR, a series of peptide analogs were prepared that were tyrosine-substituted at different positions in the peptide sequence. Then cAMP inhibition assays were performed using both the tyrosine-substituted peptides and monoiodotyrosine substituted peptides. Iodinated peptide was synthesized using the chloramine T method of Hunter and Greenwood (1962, *Nature* 194: 495). From these studies it was determined that the peptide analog having tyrosine at position 14 (Y-14: SEQ ID No.: 6) and its monoiodo form (I-Y14) were OFQR agonists of almost equivalent potency to the orphanin FQ peptide, having $EC_{50}$ values of 1 nM and 3 nM, respectively.

Figure 8:
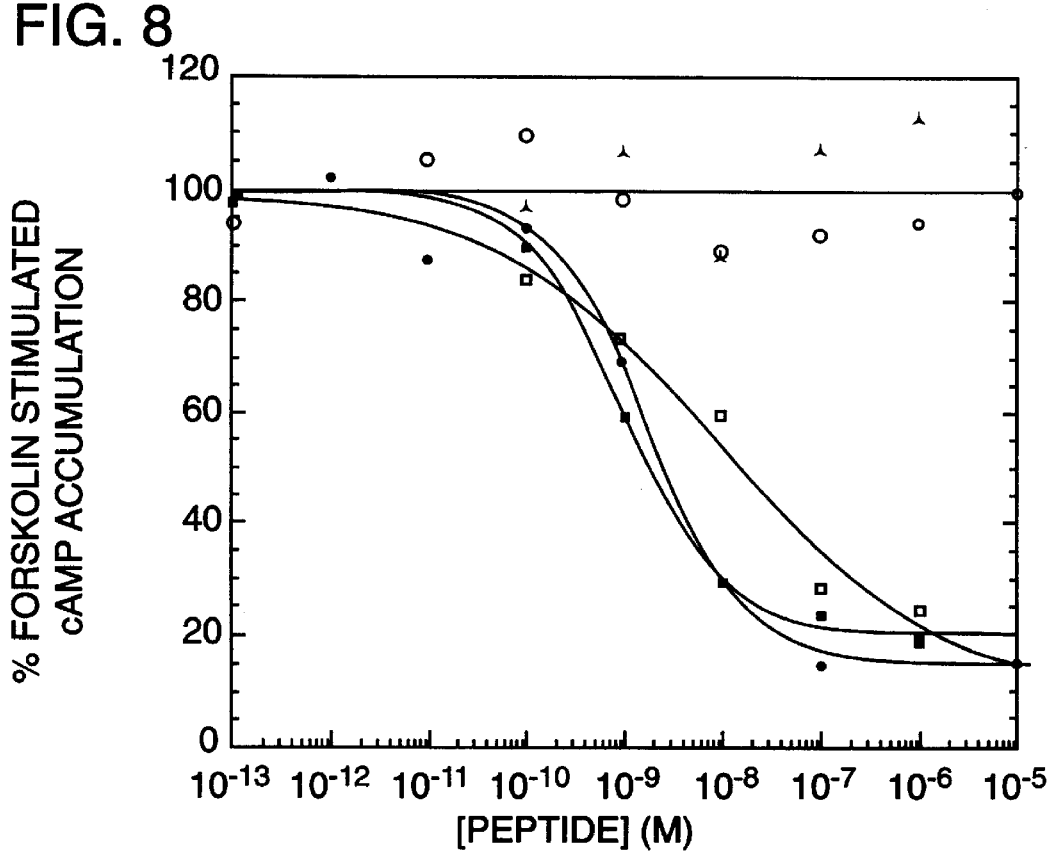
FIG. 8 is a graph illustrating the extent of inhibition of forskolin-stimulated cAMP accumulation in OFQR transfected CHO cells by the peptides orphanin FQ (filled circles); Y14-orphanin FQ (filled squares); monoiodinated Y14-orphanin FQ (open squares) and Leu-Enkephalin (open circles). Orphanin FQ-treated untransfected CHO cells are shown as filled triangles.

FIG. 8 shows a comparison of adenyl cyclase inhibitory activity of orphanin FQ (filled circles), Y14 orphanin FQ (filled squares), monoiodo Y14 orphanin FQ (open squares) and Leu-Enkephalin (open circles) in transfected CHO cells heterologously expressing OFQR; untransfected CHO cells were treated with orphanin FQ peptide as a control (filled triangles). Data were normalized so that cAMP levels in forskolin-stimulated, untransfected CHO cells was equal to 100%. cAMP levels were determined with all incubations being done at least twice in triplicate. FIG. 8 shows the results of a representative experiment.

The Y14 peptide was used to quantitatively assay receptor binding affinity for the novel ligand. Membranes from OFQR transfected CHO cells (LC-7) were used at a concentration of 55 μg membrane protein/assay. Membranes were incubated with increasing concentrations of ($^{125}$I)-Y14-orphanin FQ in a final volume of 0.2 mL binding buffer (50 mM Hepes, pH 7.4, 10 mM NaCl, 1 mM MgC12, 2.5 mM CaC12, 0.1% bovine serum albumin, 0.025% bacitracin) containing 1 mg wheat germ agglutinin-coated SA beads (Amersham). Iodinated peptide was synthesized as above using the chloramine T method. The monoiodinated species was obtained as a single peak, having a specific activity of 2200 Ci/mmole on the day of synthesis. Assays were performed in 96-well plates (OptiPlate, Caberra Packard), and the mixtures were incubated with shaking for 1 h. Bound ligand-associated radioactivity were determined by scintillation proximity (see, for example, Nelson, 1987, *Anal. Biochem.* 165: 287; Bosworth and Towers, 1989, *Nature* 341: 167) using a TopCount microplate scintillation counter (Canberra packard). Concentrations of free ligand were calculated by subtracting the amount of specifically-bound ligand from the total amount of radioligand added.

Figure 9:
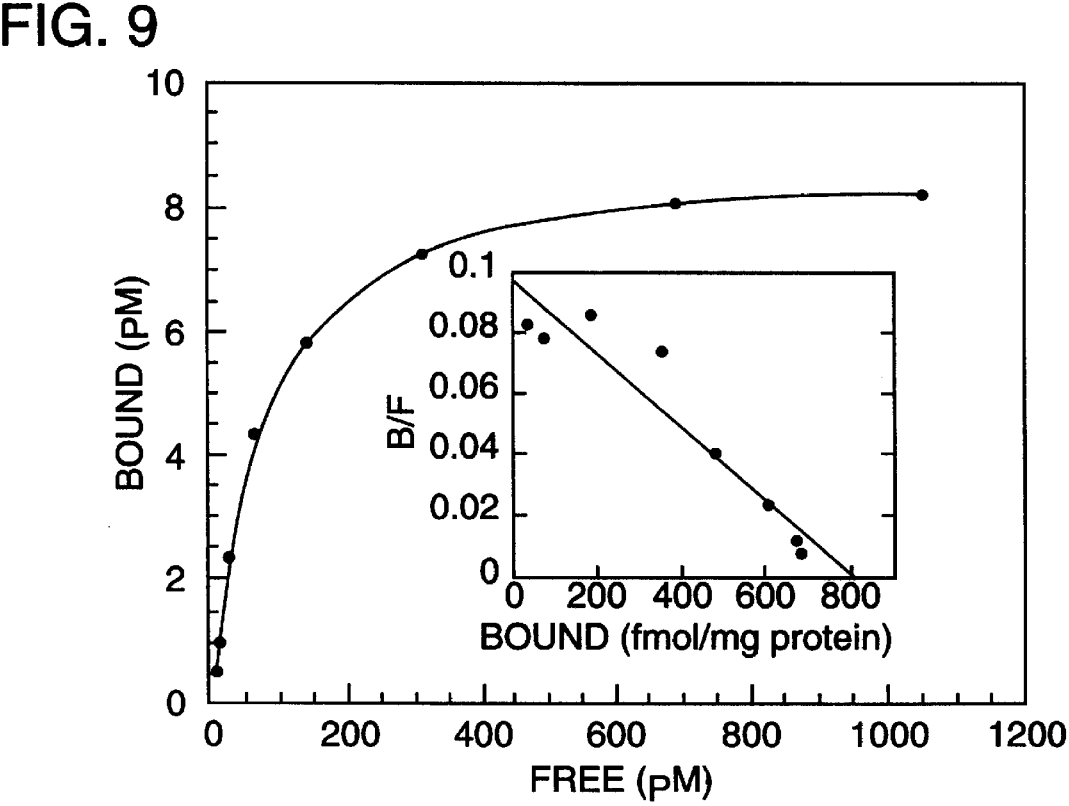
FIG. 9 is a graph of ($^{125}$I)-labeled Y14-orphanin FQ binding to isolated membranes from OFQR transfected CHO cells. The inset is a Scatchard analysis of these results.

The results of these experiments are shown in FIG. 9. A Scatchard analysis is shown in the inset. The radiolabeled monoiodo-Y14-orphanin FQ peptide displayed saturable and displaceable binding to membranes of OFQR-expressing transfected cells, having a $K_D$ (slope of Scatchard line=$-1/K_D$) of 0.1 nM (80 picomole±0.02 nanomole) and a $B_{max}$ (Scatchard line abscissa intercept) of 800 fmol/mg membrane protein. $K_D$ was determined as in Munson, Principles of Pharmacology (Chapman & Hall), 1995, Chapter 1 (which is incorporated by reference). These experiments demonstrate that the novel endogenous ligand peptide, orphanin FQ, and Y14-tyrosine substituted analogs thereof, bind saturably to OFQR with high affinity, further confirming the conclusion that this peptide is a naturally-occurring, endogenous ligand for this receptor. These experiments also indicate that the Y14-substituted peptide can be used as a radioligand to detect and quantify OFQ opioid receptor levels.

EXAMPLE 6

Functional Characterization of the Orphanin FQ Peptide

In order to study the physiological activity of the orphanin FQ peptide, the in vivo activity of the peptide was investigated on unrestricted animals, and specifically, on nociception in such animals.

Figure 10A:
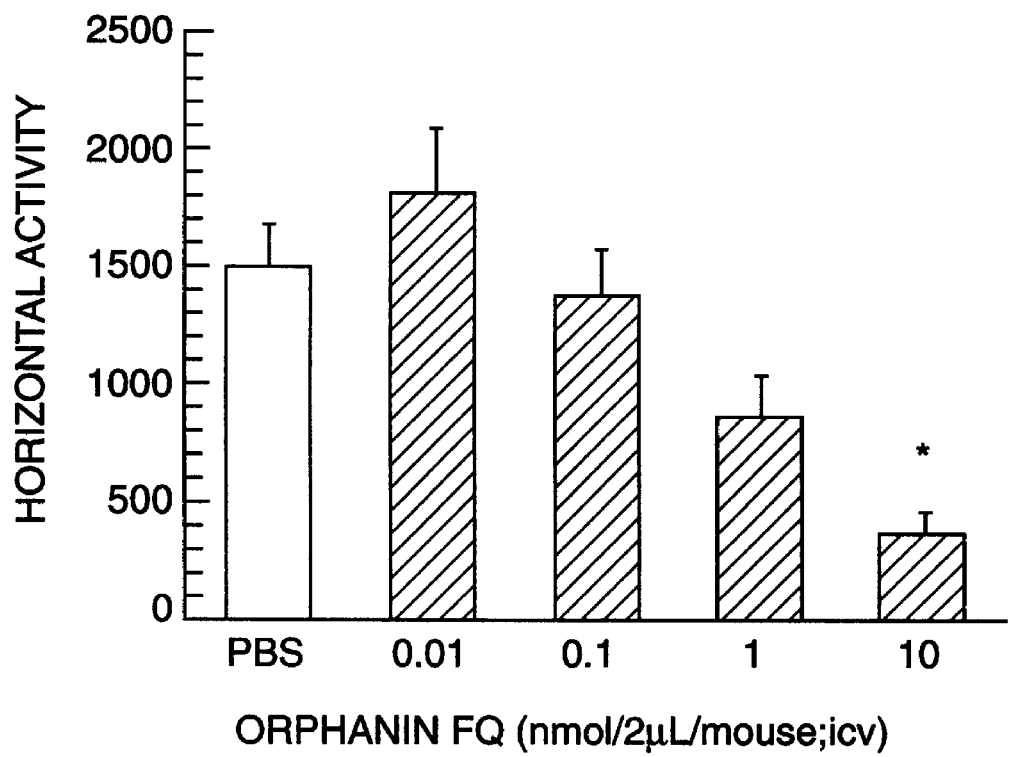
FIG. 10A shows the effects of horizontal activity in mice treated with varying concentrations of orphanin FQ peptide.
Figure 10B:
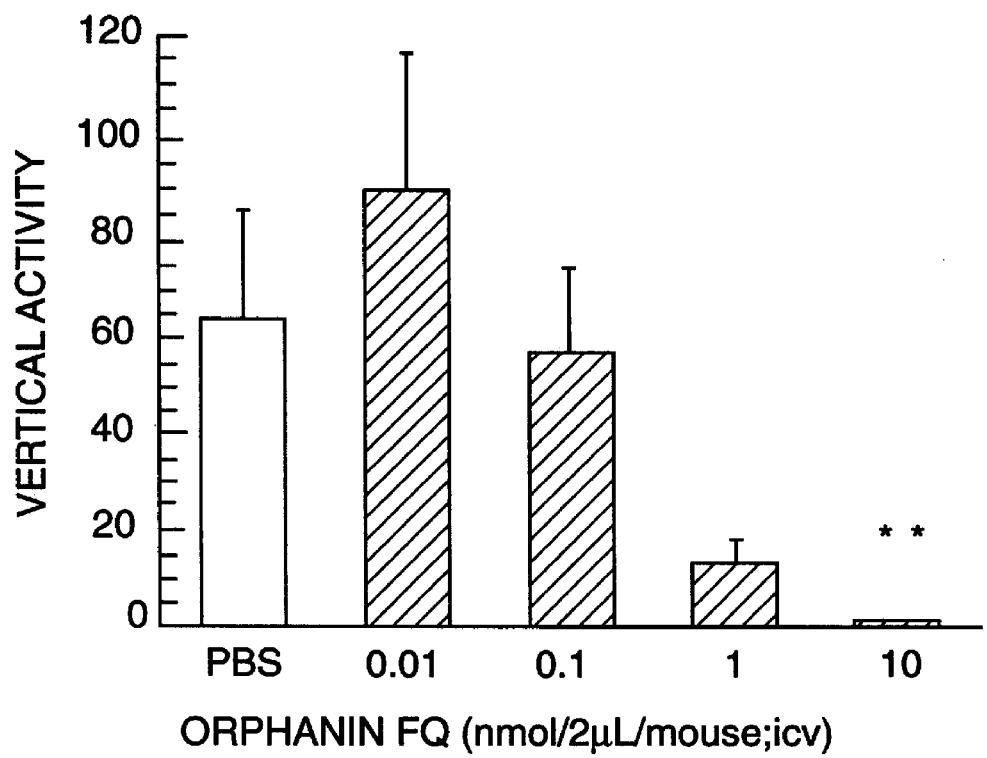
FIG. 10B shows the effects of vertical activity in mice treated with varying concentrations of orphanin FQ peptide.

For these experiments, the peptide was administered intracerebroventricularly (icv) and intrathecally (it) in mice. Immediately after peptide administration, mice were placed in transparent boxes in groups of three, and behavioral signs recorded. Emphasis was placed on signs indicative of depressant, stimulant and autonomic effects of the peptide (as described by Irwin, 1968, *Psychopharmacologia* 13: 222). In open-field observation experiments, the peptide at larger doses (e.g. above 1 nmole/2 µL/mouse) was noted to have a profound influence on locomotor activity, as well as a decrease in muscle tone, a loss of righting reflex, and ataxia. A quantitative investigation showed a decrease of both horizontal and vertical locomotion following icv administration of the peptide at concentrations of 0.1–10 nmole/2 µL/mouse. These results are shown in FIG. 10. The effects of the peptide on horizontal and vertical locomotor activity was measured using Digiscan Animal Activity Monitors (Omnitech, Columbus, Ohio). The values for horizontal and vertical locomotor activity represent the total number of interruptions of the horizontal and vertical sensors during the first 10 minutes following administration of the peptide. Data are shown as the mean ± standard error of the mean.

Figure 11:
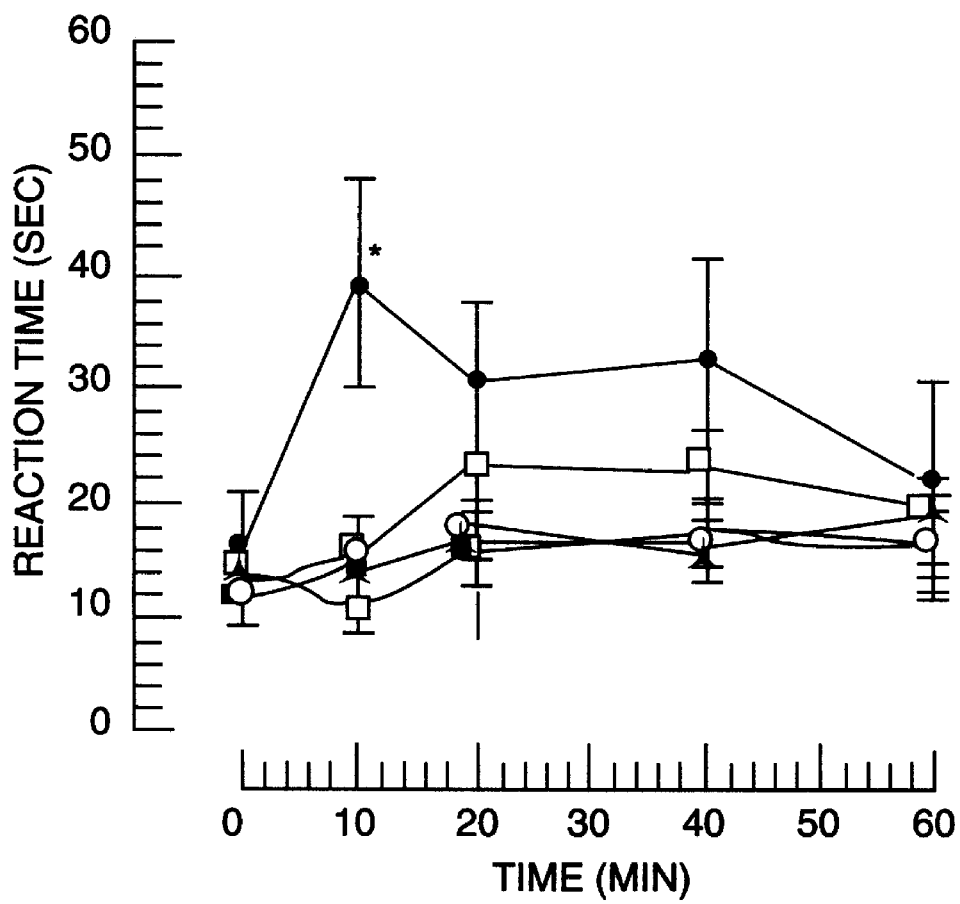
FIG. 11 illustrates the effects of orphanin FQ peptide on nociception in mice as determined using a hotplate assay.
Figure 12:
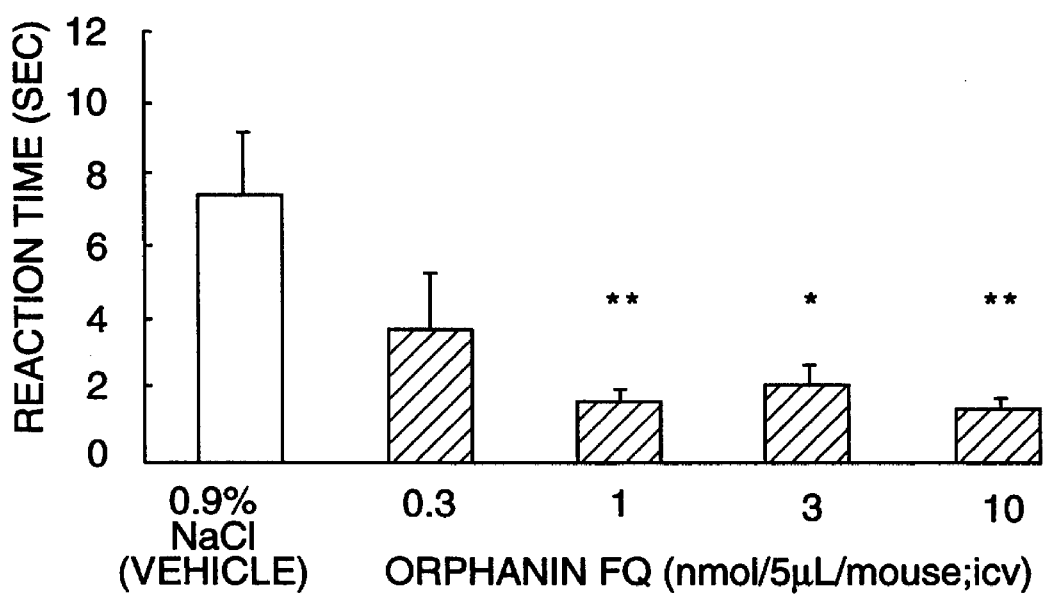
FIG. 12 shows the effects of varying icv doses of orphanin FQ peptide on nociception in mice as determined using a tail-flick assay.

On the other hand, the orphanin FQ peptide showed little analgesic effect in these mice, as recorded in a hot plate test, as shown in FIG. 11. Groups of 6–8 male MORO mice (weight=22 g) were administered phosphate buffered saline (open circles) or varying doses of the orphanin peptide. Reaction time represents the time taken for the mice to lick their paws. The hot plate was set to 58° C., and a cutoff time of 60 sec was used. No significant decrease in reaction time was detected, with the exception of mice administered the highest levels of peptide, 10 nmole/mouse, icv (about 0.45 nmole/g) designated by an asterisk. This observation was most likely related to a decrease in locomotor activity and muscle tone. At all doses tested, all animals exhibited normal toe- and tail-pinch reflexes, as shown in FIG. 12. No analgesic effect was observed when orphanin FQ was administered intrathecally at 2.5–10 nmole/4 µL/animal; however, at the highest dose, hind limb paralysis and decrease in locomotor activity was observed. No analgesic effect was observed in any mouse with this peptide at doses that did not produce significant decreases in motor activity and muscle tone. These results indicate that, despite structural homology with analgesia-producing opioid receptor ligands as described in Example 5, the orphanin FQ peptide appears to be pharmacologically distinct and to lack appreciable analgesic activity (which is defined as no significant decrease in reaction time as measured in this Example 6).

EXAMPLE 7

Stress Induced Analgesia Reversed by Naloxone and OFQ

In spite of the structural homology between OFQ and the opioid peptides, icv injected animals do not display unconfounded antinociception or analgesia, which would be observable as a decreased sensitivity to pain. One report has been made that OFQ instead induces hyperalgesia, a supersensitivity to pain, in both the tail flick and hot-plate assays. Meunier et al., Nature 377,532–535 (1995). Contrary to the expectations of others, the present inventors have found that OFQ does not produce hyperalgesia, but instead potently and dose-dependently antagonizes opiate actions such as analgesia. Hence OFQ is observed to act as an endogenous anti-opioid peptide that is capable of reversing effects of either endogenous or exogenous opioids in an animal, such as a mouse or human.

Figure 13A:
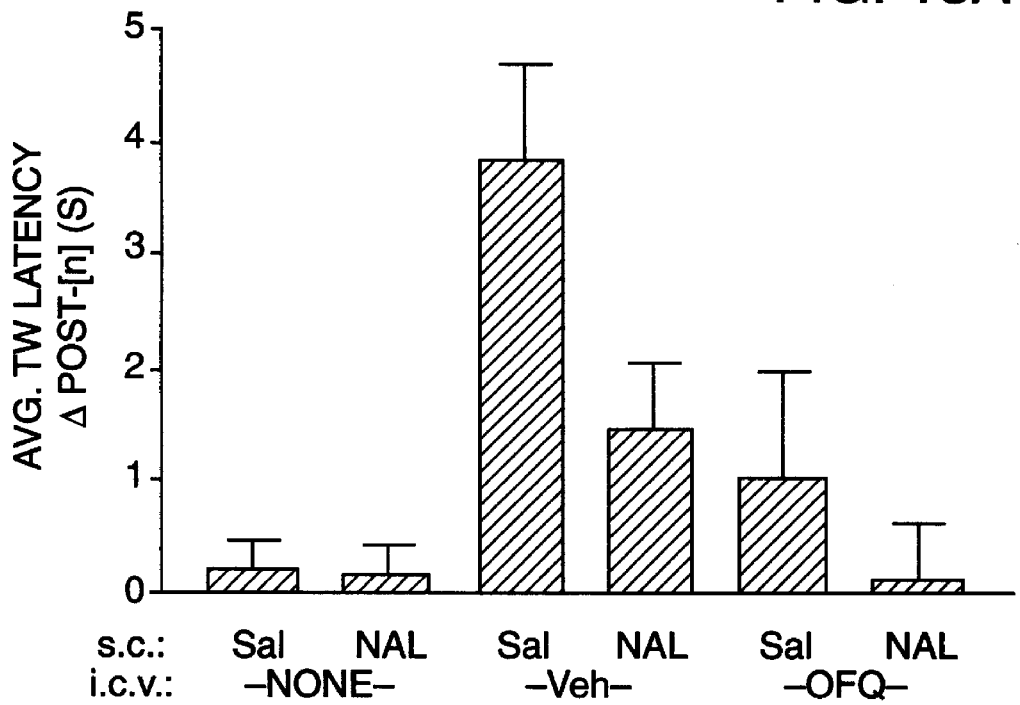
FIG. 13A is a bar graph, illustrating the anti-opioid effect of OFQ on stress induced analgesia, showing average tail withdrawal latency change in animals that have not received morphine analgesia, after administration of saline, naloxone, and OFQ.

The anti-opioid effects of the OFQ peptide are demonstrated in this example, which shows the effects of OFQ in the tail-withdrawal (TW) test, an assay of response to acute thermal pain. The results are shown in FIG. 13A. Swiss-Webster mice of both sexes (20–35 g; Simonsen Inc.; N=7–8 per group) were tested for nociceptive sensitivity to immersion of the distal half of the tail in 46° C. water before and after (10, 20 and 30 min) subcutaneous (sc) injection with saline (Sal; 10 ml/mg) and naloxone (NAL, 1 mg/kd) and icv injection (under light halothane anesthesia) with Veh (2.5 microliter of artificial cerebrospinal fluid (CSF)) or 10 nmole OFQ. Separate groups of mice received only sc injections of saline or naloxone (labeled None to indicate no icv injection in FIG. 13A).

The latency to respond to the heat stimulus by a vigorous flexion of the tail was measured to the nearest 0.1 s by an experienced observer blind to the drug condition of the animal. Mice were lightly restrained in a cloth/cardboard holder during testing. In the absence of a withdrawal reflex or other indication of distress, the tail was removed from the water after a cut-off latency of 15 s. To improve accuracy, three separate TW latency determinations, separated by 20 s, were made and averaged at each test. In this and all subsequent experiments, no main effects nor interactions of sex were found to be significant, so data from both sexes were pooled. Because there were no changes in post-injection TW latencies in any group with repeated testing at 10, 20 and 30 min post-injection, data from these time points were pooled. An ANOVA (analysis of variants) performed on averaged TW change data revealed significant main effects of sc injection and icv injection (F2,44=9.31, p<0.05, respectively). Planned contrasts demonstrate that the Sal/Veh group is significantly different from all others.

Although there was no evidence of hyperalgesia produced by OFQ, vehicle-treated animals displayed higher TW latencies (ie were less sensitive to pain) than OFQ-treated animals (p<0.01) (FIG. 13). The vehicle treated animals were displaying stress-induced-analgesia (SIA). SIA is mediated by endogenous opioids, hence the effect of both the opiate antagonist naloxone and OFQ on the SIA was investigated. Naloxone and OFQ both attenuated the 4 s post-injection increase in TW latency displayed by vehicle-treated animals (p<0.05). The combined administration of naloxone and OFQ had no additional effect. In no case did any mouse treated with OFQ or naloxone exhibit hyperalgesia; administration of these drugs instead merely returned pain sensitivity to baseline by reversing SIA. Hyperalgesia would have been detected by a shorter tail withdrawal latency than with vehicle alone, which was not observed with OFQ.

EXAMPLE 8

Reversal of Morphine Analgesia by OFQ in Writhing Test

To maximize the observation of hyperalgesia, the acetic acid AC assay was performed to determine the effect of OFQ on the abdominal constriction test. This test is an extremely sensitive measure of tonic, chemically-induced pain stimulus. The results are given in FIG. 13B.

The AC assay was a modification of the technique originally described by Koster et al. Mice (N=9–15 per group) were acclimated to individual cylindrical Plexiglass observation chambers for >30 minutes. They were then weighed and given an sc injection of saline (Sal; 10 ml/mg) or naloxone (NAL; 1 mg/kg and 10 mg/kg), or handled but given no injection (None). Immediately thereafter, mice were lightly anesthetized with halothane and given and icv injection of vehicle (VEH; 2.5 $\mu$l of artificial CSF) or 2.5 nmole OFQ in 2.5 $\mu$l vehicle (OFQ-2.5). A separate group of Sal-treated mice received no icv injection (None). Between 5 and 10 minutes later, all mice were given an intraperitoneal (ip) injection of 0.9% acetic acid and placed back in their observation chambers. For the next 30 minutes, the number of abdominal constrictions (lengthwise stretches of the torso with a concomitant concave arching of the back) were counted and recorded. Four mice in separate chambers were observed simultaneously by a single experimenter blind to drug condition. ANOVA revealed a significant group differences.

Figure 13B:
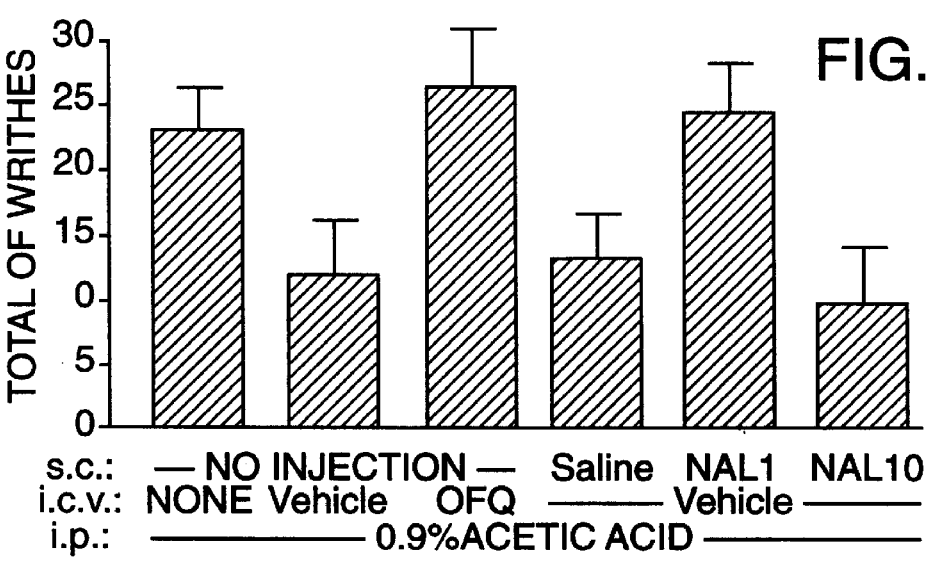
FIG. 13B is a bar graph showing the results of a writhing test, demonstrating reversal of morphine analgesia by OFQ.

The results are shown in FIG. 13B. The decreased number of constrictions in VEH mice is believed to be due to SIA, which was reversed by NAL and OFQ-2.5. The 2.5 nmole icv dose of OFQ was pharmaceutically sufficient to inhibit the analgesic effect of morphine within 30 minutes after the OFQ was administered.

EXAMPLE 9

Reversal of Morphine Analgesia by OFQ in Tail Withdrawal Latency

OFQ reverses the analgesic actions of morphine, which are mediated by the opioid SIA substrate. In this example, morphine is administered to mice immediately following assessment of their baseline nociceptive sensitivity. It produced a profound analgesia that peaked at 30 minutes post-injection (FIG. 14) and lasted about 2 hours. But OFQ reversed this analgesia in a dose-dependent manner (at doses of 2.5–25 nmole).

Swiss-Webster mice of both sexes (N=6–11 per group) were tested for baseline nociceptive sensitivity on the 49° C. TW test (as described in Example 7), injected s.c. with morphine sulfate (MOR; 5 mg/kg), and then retested 20 min later to establish the existence of morphine analgesia. Analgesic mice (those with TW latencies of at least double their baseline; all except 3) were then lightly anesthetized with halothane, injected i.c.v. with vehicle (Veh; 2.5 $\mu$l artificial CSF) or OFQ (2.5, 5, 10 or 25 nmole in 2.5 $\mu$l vehicle), and retested for TW latencies 10, 25, 40 and 100 min later by an experimenter blind to OFQ dose. The 25 nmol OFQ dose produced marked atonia and flaccid paralysis in up to 50% of mice. These side-effects should not, however, be considered a confound of the present data because mice injected with this high OFQ dose actually reacted faster to the thermal stimulus.

FIG. 14 shows time-course data demonstrating morphine analgesia and its dose-dependent reversal by four doses of OFQ. Symbols represent mean (±SEM) TW latencies from 49° C. water at each time point.

A linear regression analysis was used to calculate the dose of OFQ causing a 50% inhibition of the effect of 5 mg/kg morphine analgesia, and determined that this $ED_{50}$ was 7.5 nmol in a 2.5 $\mu$l volume. The $ED_{50}$ is the dose required to produce a response of 50% of maximal effect. A significant inhibition of analgesia would be a 50% inhibition of opiate analgesia. The $ED_{50}$ would be a pharmaceutically sufficient amount of OFQ to achieve significant inhibition.

EXAMPLE 10

Attenuation of Morphine Hypothermia by OFQ

This example demonstrates the ability of OFQ to functionally antagonize opioid effects other than analgesia. The non-nociceptive action of morphine studied here was the ability to induce hypothermia in rodents at high doses. The DBA/2J mice strain was used to study attenuation of hypothermia because of its known robust hypothermic response.

Core body temperature of DBA/2J mice (15–30 g; The Jackson Laboratory; N=7–8 per group) was assessed immediately before and 30 min after systemic administration of saline (Sal; 10 ml/kg) or morphine (MOR; 20 mg/kg, i.p.). Immediately thereafter, mice were injected i.c.v. with vehicle (Veh; 2.5 $\mu$l artificial CSF) or 5 or 10 nmole OFQ in 2.5 $\mu$l vehicle (OFQ-5 and OFQ-10), and retested 15, 30 and 60 min later.

Figure 15:
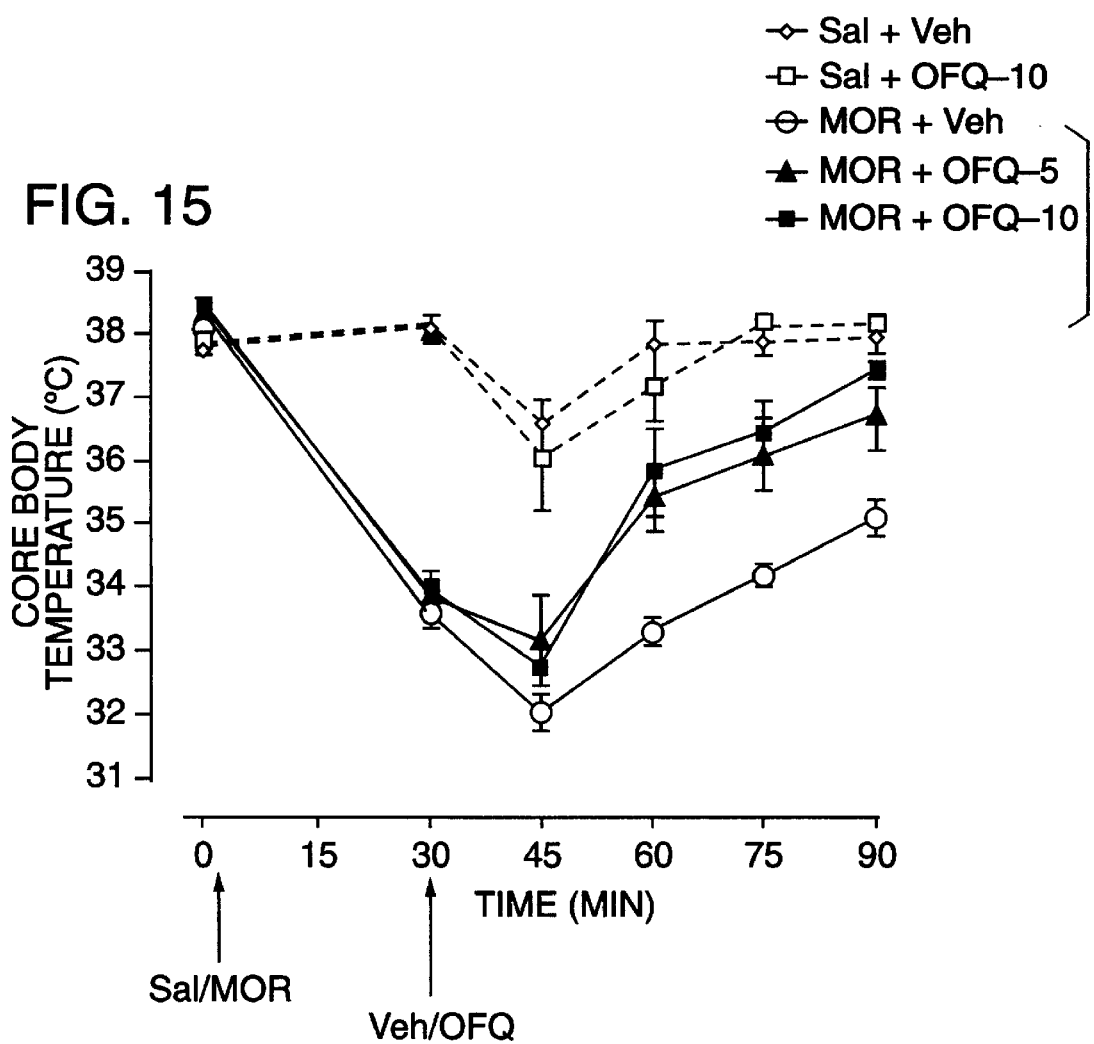
FIG. 15 is a graph of core body temperature vs. time, demonstrating attenuation of morphine hypothermia by OFQ.

As shown in FIG. 15, there was a 6° C. decrease in body temperature produced by MOR, in addition to a transient hypothermia produced by halothane. The body temperature of saline-treated mice remained constant at about 38° C., except for a brief hypothermic episode from exposure to halothane. OFQ itself did not affect body temperature. However, both doses of OFQ significantly reversed 20 mg/kg MOR hypothermia at 60–90 minutes post-MOR injection ($F_{4,33}$=44.94,p<0.001). A reversal of hypothermia would be at least a 1° C. increase in temperature under these conditions. The dose of OFQ given in this Example is pharmaceutically sufficient to achieve this reversal.

The high dose of morphine (20 mg/kg) used in this experiment produced Straub tail, which is a muscular rigidity of the tail accompanying exposure to opiates in virtually all mice. Exposure to doses of at least 5 nmole OFQ effectively eliminated Straub tail in the vast majority of animals within 1–2 minutes following icv injection. The 5 nmole icv dose in the 15–30 g rat would be an example of a pharmaceutically sufficient amount to eliminate Straub tail in a majority of animals within 1–2 minutes following icv injection. This finding further generalizes OFQ's functional antagonism of opiate mechanisms.

EXAMPLE 11

Precipitation of Opiate Withdrawal Syndrome in Morphine Dependent Mice

Opiate tolerance, dependance and withdrawal can not be explained by simple alterations in opiate receptor function. Morphine tolerance and addiction is believed to involve action of (until-now) ill-defined anti-opioid activities. Specifically, morphine administration is believed to cause the release of anti-opioid peptides, which in turn may counteract the effects of morphine and contribute to maintenance of physiologic homeostasis. An anti-opioid peptide should precipitate withdrawal symptoms by interfering with this homeostatic state. This Example illustrates that OFQ indeed causes an opiate withdrawal syndrome in morphine dependent mice, further supporting its role as an anti-opioid.

C57BL/6J mice of both sexes (15–25 g; The Jackson Laboratory; N=6–11 per group) were made dependent on morphine using a sustained-release preparation. The preparation was 35 mg/ml morphine sulfate in saline solution, vortexed with a 6:1 light mineral oil; mannide monooleate (Arlacel A, Sigma) mixture in a 1:7 ratio of morphine:oil solution. The viscous white emulsion was administered s.c. at a dose of 200 mg/kg morphine (in an 8 ml/kg volume) using a 21-gauge needle. At the time of testing (5–6 h post-injection) morphine was still present based on Straub tail and 49° C. TW latency elevations. Mice were administered s.c. saline (Sal; 10 ml/kg) or NAL (10 mg/kg) followed immediately by i.c.v. vehicle (Veh; 2.5 μl artificial CSF) or OFQ (0.1–10 nmole in 2.5 μl vehicle). Since all doses of OFQ used appeared to be equally effective in the precipitation of withdrawal, these data were combined. Each animal was then placed on individual 17×27 cm platforms suspended 32 sm above a table top. The number of jumps was recorded for 20 min, as were occurrences of tremor/ "wet-dog shakes" and the presence of ptosis. OFQ doses >5 nmole produced atonia in some morphine-dependent mice that may have hindered jumping behavior.

Figure 16:
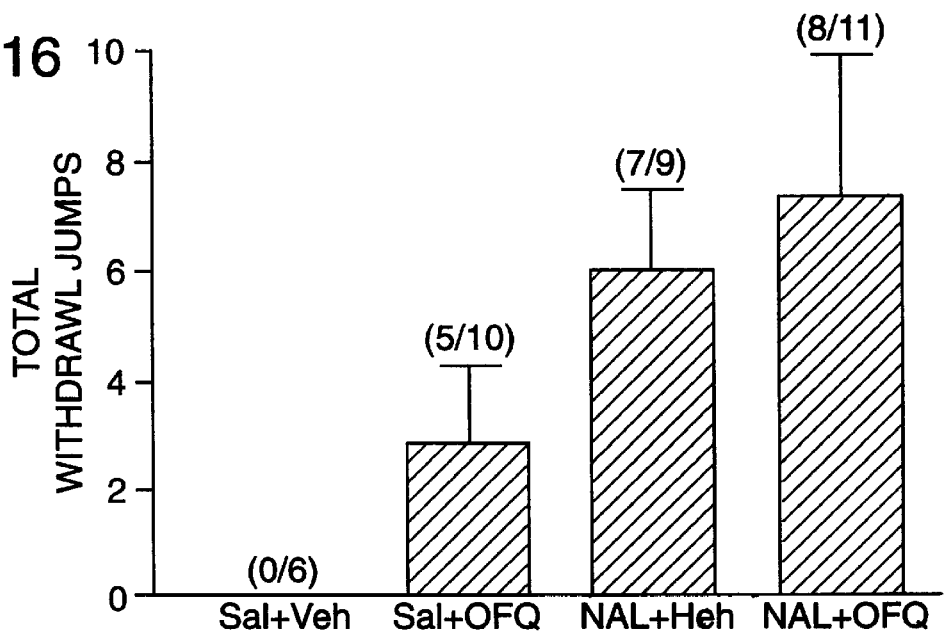
FIG. 16 is a graph of withdrawal jumping precipitated by OFQ in morphine dependent mice, demonstrating precipitation of withdrawal signs in the mice.

Withdrawal jumping precipitated by OFQ is shown in FIG. 16. Bars represent mean (±SEM) number of withdrawal jumps in the 20-min testing period. Ratios above the error bars describe the number of animals exhibiting jumping behavior relative to the total number tested. The withdrawal syndrome produced by i.c.v. OFQ was unequivocal, albeit modest in comparison to that produced by systemic naloxone (NAL). Other withdrawal symptoms, including wet-dog shakes and ptosis, were observed in mice treated with OFQ, but not in mice merely given injections of vehicle. Precipitation of withdrawal shall be defined as increasing total withdrawal jumps in the protocol of Example 11.

EXAMPLE 12

Determination of Affinity of OFQ Receptor Agonists

The peptide of the present invention does not bind with high specificity to μ, κ or δ opioid receptors. This example will demonstrate that lack of receptor specificity, and demonstrate how specificity of ligand-receptor binding can be determined. [$^3$H]diprenorphine was used as a competitive antagonist to assay receptor binding affinity for OFQ. Membranes from OFQR transfected CHO cells ((LC-7) were used at a concentration of 100 μg membrane protein/assay.

Stable transfected-CHO cells were rinsed three times with 50 mM Tris-HCl buffer (pH 7.7), harvested and homogenized in the same buffer using a glass-Teflon homogenizer at 4° C. The homogenate was centrifuged at 42,000 g at 4° C. for 15 minutes. The pellet was resuspended in 50 mM Tris-HCl buffer and incubated at room temperature for one hour. Following pre-incubation, the homogenate was centrifuged as described above and the pellet was stored at 70° C. until used.

The pellet was thawed, washed with 50 mM Tris-HCl buffer and the homogenate was centrifuged as above. The pellet was resuspended in the binding buffer and the protein concentration was adjusted to 100 μg/μl as determined by a standard curve determined by Lowry assay using bovine serum albumin as the standard. In equilibrium competition experiments [$^3$H]diprenorphine was utilized as an antagonist radioligand to label μ, κ and δ receptors, respectively, in CHO cells expressing the μ, κ or δ receptors, and OFQ was used as a displacer. In addition, DAMGO, U50488H and DPDPE were also used as a displacer in the μ, κ and δ receptor expressed CHO cells in these assays.

Binding reactions were conducted in an incubation tube with 50 mM Tris-HCl buffer (pH 7.7) in the presence of 10 micromolar peptidase inhibitor bestatin at 25° C. for 60 minutes in a total volume of 1 ml using a final [$^3$H] diprenorphine concentration of 0.36 nM. All of the tubes contained the membrane preparation and [$^3$H]diprenorphine. A ligand of interest was also added to each membrane/ diprenorphine preparation. A subset of the tubes contained 10 micromolar naloxone as the ligand of interest, to permit determination of non-specific binding. Another subset of the tubes contained OFQ in the presence of the [$^3$H] diprenorphine to determine displacement of OFQ from each class of receptor by the diprenorphine displacer. Another subset of tubes contained DPDPE, while yet another subset contained U50488H as the ligand of interest. Each of the ligands of interest was present in a concentration from zero in order of magnitude up to 100 micromolar. The concentration of radioactive diprenorphine displacer was varied, in different sets of tubes, across the range shown in FIG. 17.

At the end of the 60 minutes period of incubation, the incubation was terminated by vacuum filtration using a Brandel CellHarvester over polyethylenimine (0.5%)-soaked GF/B filters. The Cell Harvester has a manifold that simultaneously emptied out all of the reaction tubes in a controlled manner and deposits the contents on a filter disk that corresponds to each tube, washed 2 times with 2 ml each of ice-cold 50 mM Tri-HCl buffer, and the contents again deposited on the corresponding filter disk. Filter disks were placed in minivials, allowed to elute overnight in EcoLume scintillation fluid (ICN, Costa Mesa, Calif.), and then counted in a Beckman scintillation counter.

Figure 17A:
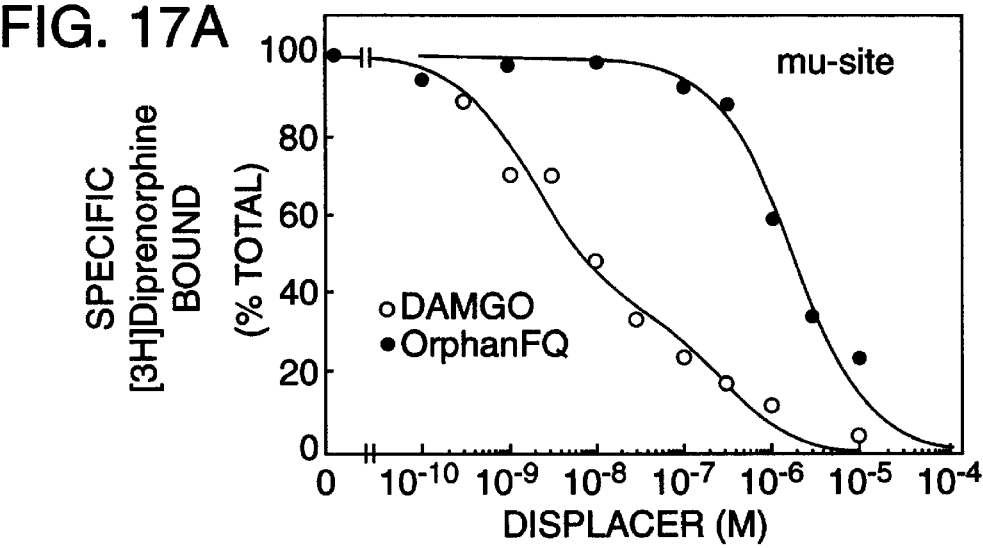
FIGS. 17A, 17B, and 17C is a series of graphs showing that OFQ does not bind with high affinity to mu, delta and kappa opioid receptors.
Figure 17B:
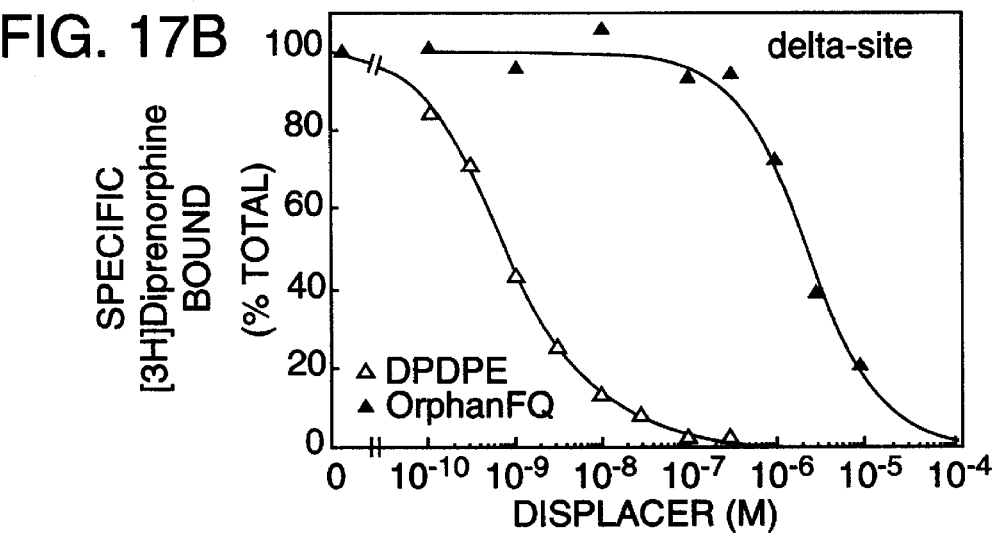
Figure 17C:
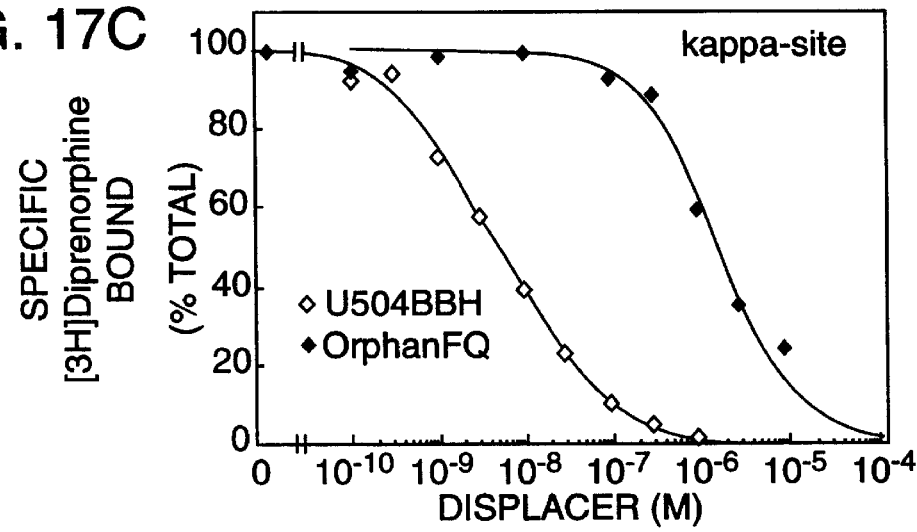

The resulting data were radioactive counts, which were proportional to percent total bound diprenorphine radioligand. The percent bound ligand of interest (e.g., OFQ) was inversely proportional to the amount of radioactivity detected. As shown in FIG. 17, the percent of total OFQ at the μ, κ and δ receptors was stable over a broad range of displacer concentrations. The DAMGO, DPDPE and U50488H ligands (known to bind to the μ, κ and δ receptors) were, however, competitively displaced.

For each set of ligand displacement studies, the results obtained with the scintillation counter were analyzed using an IBM computer system equipped with a GraphPad Inplot (from GraphPad, Inc., of San Diego, Calif.) software program. This program performs a nonlinear regression fit of a logistic equation to the data, and produced the graphs shown in FIG. 17.

Using this data, the program further computes $IC_{50}$ (the concentration of unlabeled ligand, such as OFQ) that inhibits 50% of the radioactively labeled ligand binding, such as [$^3$H]diprenorphine). $IC_{50}$ and $K_i$ are related by the equation $K_i = IC_{50}/(1+[L]/K_D)$ where [L] is the concentration of labeled ligand diprenorphine, and $K_D$ is defined as the dissocation constant for [$^3$H]diprenorphine. $IC_{50}$ data are shown in the following Table 1:

TABLE 1

Affinity of opioid receptor agonists and OFQ at mu, delta and kappa receptors expressed in CHO cells

| Compound | $IC_{50}$* (nM) | | |
|---|---|---|---|
| | $\mu$-site | $\delta$-site | $\kappa$-site |
| DAMGO | 2.0 ± 0.1 | | |
| DPDPE | | 0.59 ± 0.01 | |
| U50488H | | | 1.6 ± 0.2 |
| OrphanFQ | 2083 ± 432 | 2246 ± 339 | 754 ± 89 |

*$IC_{50}$ values were derived from competition experiments using an opioid antagonist radioligand [$^3$H] diprenorphine (0.36 nM).

Data are mean SE values derived from three independent experiments. The ligand of interest has a low $IC_{50}$ ($\leq 100$ nM) if it binds with high affinity to the receptor. All ligands of interest bound with high affinity to one of the opioid receptors, except for OFQ which had an $IC_{50}$ greater 2000 at $\mu$ and $\delta$, and 754 at the $\kappa$ site. These values show that OFQ does not specifically bind to $\mu$, $\kappa$ and $\delta$ receptors. As used herein, specifically binding to a receptor shall mean having an affinity expressed by an $IC_{50}$ of less than about 100 nm. In preferred embodiments, the affinity is 0.1–10 nm, preferably less than 1 nm, and most preferably less than 0.1 nm.

EXAMPLE 13

The affinity of any of the peptides of the present invention can be determined by an affinity study as described in Example 12. Hence, an OFQ analogue with amino acid substitutions can be substituted for the OFQ of Example 12. An OFQR transfected CHO cell membrane would be substituted for the $\mu$, $\kappa$ and $\delta$ receptor expressing cell membranes of Example 12 to determine affinity of the peptide analogue to the OFQ receptor. This provides a straightforward screening method for determining whether the peptide binds specifically ($K_i$ or $IC_{50} \leq 100$ nm) to the OFQR.

EXAMPLE 14

Protocol for Obtaining OFQ Anti-Opioid Antagonist and Using the Antagonist

Antagonism of the OFQ/OFQR system will have substantial clinical utility. Although the antagonist will not have analgesic actions itself, it is expected to be effective as an adjunct to morphine pharmacotherapy. By interfering with the body's homeostatic anti-opioid mechanism, the OFQR antagonist is expected to allow use of lower therapeutic doses of morphine to achieve greater analgesic effects. Lower doses of morphine have the advantage of producing fewer side-effects (such as respiratory depression or constipation), and will also help avoid development of tolerance or addiction that can be experienced following prolonged use of high doses of morphine. The OFQR antagonist is also expected to lessen the signs and symptoms of opiate withdrawal in addicts. Use of the antagonist in this manner has been made possible by the present inventors' recognition that the OFQ/OFQR interaction mediates an anti-opioid effect.

Although a method of using an anti-opioid antagonist has not been known to the art, oligonucleotides have previously been reported that antagonize the effect of OFQ. See Meunier et al., Nature 377: 532–535 (1995), which is incorporated by reference. The oligonucleotides reported in that paper were antisense oligonucleotides to translated regions of the OFQR. Antisense oligonucleotide mAS[25,9] was the 17-mer 3'-GGAGAAAGGACGGGGTA-5' complementary to bases 9–25 of the translated region of the mouse $ORL_1$ mRNA. Control missense oligonucleotide hAS[25,9], was the 17-mer 3'-GGAGAAGGGGCGCGGCA-5' complementary to bases 9–25 of the translated region of the human $ORL_1$ mRNA. The oligonucleotides were dissolved in sterile physiological saline at the final concentration of 2 mg ml. Male Swiss CD1 mice (20–25 g; Charles River) were manually injected with 10 $\mu$l of solution directly into the lateral brain ventrical every day for 4 consecutive days.

Expression of the receptor was inhibited by the antisense oligonucleotides. Other oligonucleotides of similar length could be mapped to bases 9–25 (using the genetic code of Table 1) to provide similar antagonistic activity.

Other antagonists are used in the present method to treat an opiate withdrawal syndrome. A heptadecapeptide is synthesized with a sequence that is substantially homologous to the OFQ amino acid sequence, but with one or more amino acid substitutions made. The synthesized heptadecapeptide (or other oligopeptide) is then screened using the cAMP accumulation assay in OFQ transfected CHO cells. Peptides that do not inhibit cAMP accumulation (using the assay described in Example 5) are then selected as a partial agonist that acts as an antagonist. The selected peptides obtained by this straightforward assay are then administered to animals (as in Example 11) to demonstrate attenuation of opate withdrawal, as evidenced by reduction in withdrawal jumping compared to animals not receiving the OFQ antagonist.

Synthetic peptide combinatorial libraries may also be screened to find an agonist-antagonist peptide that does not inhibit cAMP accumulation in the disclosed assay. Screening is performed using the techniques described in Houghten et al., Generation and use of synthetic peptide combinatorial libraries for basic research and drug discovery, Nature 354: 84–86, incorporated by reference. The soluble, nonsupport bound peptide libraries appear useful in virtually all in vitro and in vivo assays, as reported by Ostresh, "Libraries from libraries: Chemical transformation of combinatorial libraries to extend the range and repertoire of chemical diversity," PNAS. The successful use of these libraries has been reported for the development of receptor-active opioid peptides. See Dooley, "An All D-Amino Opioid Peptide with Central Analgesic Activity from a Combinatorial Library," Science 266: 2019–2022, 1994, which is incorporated by reference.

Antagonists discovered by these techniques are tested for interference with opiate withdrawal signs, as in Example 8.

It should be understood that the foregoing disclosure emphasizes certain specific embodiments of the invention and that all modifications or alternatives equivalent thereto are within the spirit and scope of the invention as set forth in the appended claims.

What we claim is:

1. A method of antagonizing a physiological effect of an opioid in an animal, comprising administering to the animal a pharmaceutically effective amount of a peptide that has an activity of binding to a mammalian Orphanin FQ receptor with high specificity, wherein the peptide has an FGGF (SEQ ID No. 11) motif.

2. The method of claim 1 wherein the peptide has an amino-terminal FGGF (SEQ ID No. 11) motif.

3. The method of claim 1 wherein the peptide does not bind to mu, delta, or kappa opioid receptors with high specificity.

4. The method of claim 1 wherein the peptide antagonizes opioid analgesia without increasing nociceptive sensitivity.

5. The method of claim 1 wherein the mammalian OFQ receptor is encoded by the DNA molecule set forth in SEQ. ID. No. 3.

6. A method of antagonizing physiologic effects of an opioid in an animal, comprising the step of administering to the animal an amount of an anti-opioid peptide sufficient to reduce a physiological effect of the opioid, wherein the peptide:
   (a) has an FGGF (SEQ ID No. 11) motif;
   (b) binds with high specificity to a receptor encoded by SEQ. ID No. 3;
   (c) does not bind to mu, delta or kappa opioid receptors with high specificity; and
   (d) antagonizes opioid analgesia without increasing nociceptive sensitivity.

7. The method of claim 6, wherein the peptide antagonizes opiate induced hypothermia in animals.

8. The method of claim 6, wherein the peptide is administered to the animal to antagonize morphine induced analgesia.

9. The method of claim 6 wherein the FGGF (SEQ. ID. No. 11) motif is an amino-terminal motif.

10. The method of claim 6, wherein the peptide is a heptadecapeptide.

11. The method of claim 1 wherein the peptide is selected from the group consisting of amino acid sequences selected from the group consisting of Phe-Gly-Gly-Phe-Thr-Gly-Ala-Arg-Lys-Ser-Ala-Arg-Lys-Leu-Ala-Asn-Gln (SEQ. ID. No. 5) and Phe-Gly-Gly-Phe-Thr-Gly-Ala-Arg-Lys-Ser-Ala-Arg-Lys-Tyr-Ala-Asn-Gln (SEQ. ID. No. 6).

12. The method of claim 1, wherein the peptide is an analogue, derivative or mimetic of the peptide of claim 11.

13. The method of claim 6, further comprising administering to the animal a second anti-opioid antagonist, wherein the second anti-opioid antagonist and anti-opioid peptide are administered in a sufficient amount in combination to antagonize physiological effects of the opioid.

14. A method of antagonizing a physiologic effect of morphine in an animal, comprising the step of administering to the animal, in a sufficient amount to diminish the physiologic effect, a peptide having an amino acid sequence consisting of Phe-Gly-Gly-Phe-Thr-Gly-Ala-Arg-Lys-Ser-Ala-Arg-Lys-Leu-Ala-Asn-Gln (SEQ. ID. No. 5).

15. A pharmaceutical dosage form of the peptide of claim 1.

16. The pharmaceutical dosage form of claim 15, comprising the peptide and a pharmaceutical carrier.

17. The pharmaceutical dosage form of claim 15, further comprising instructions for administering the pharmaceutical dosage form to an animal to diminish opioid intoxication.

18. A method of antagonizing opioid effects caused by exogenous administration of an opioid in an animal, comprising administering to the animal a pharmaceutically effective amount of an anti-opioid peptide sufficient to reduce analgesia induced by the exogenous opioid, wherein the anti-opioid peptide:

(a) is a heptadecapeptide having an aminoterminal FGGF motif;

(b) binds to a receptor encoded by SEQ. ID. No. 3 with an $IC_{50}$ of 100 nm or less;

(c) does not bind to mu, delta or kappa opioid receptors with an $IC_{50}$ of 100 nm or less;

(d) antagonizes opioid analgesia without increasing nociceptive sensitivity; and (e) antagonizes morphine induced hypothermia in animals when given at a pharmaceutically effective dose to inhibit a morphine induced hypothermic response.

19. The method of claim 18 wherein the exogenous opioid is morphine.

20. The method of claim 1 wherein the peptide comprises a sequence selected from the group consisting of Phe-Gly-Gly-Phe-Thr-Gly-Ala-Arg-Lys-Ser-Ala-Arg-Lys-Leu-Ala-Asn-Gln (SEQ. ID. No. 5) and Phe-Gly-Gly-Phe-Thr-Gly-Ala-Arg-Lys-Ser-Ala-Arg-Lys-Tyr-Ala-Asn-Gln (SEQ. ID. No. 6), and substitutional variants having one or more conservative amino acid substitutions.

21. A method of antagonizing a physiological effect of an opioid in an animal, comprising administering to the animal a pharmaceutically effective amount of a peptide that has an activity of binding to a mammalian Orphanin FQ receptor with high specificity, wherein the peptide has an FGGF (SEQ. ID. No. 11) motif, or an FGGF motif having conservative amino acid substitutions in that motif which still retain the activity of binding to the receptor with high specificity.

* * * * *